(12) United States Patent
Kothakonda et al.

(10) Patent No.: US 9,382,272 B2
(45) Date of Patent: Jul. 5, 2016

(54) METHODS OF MAKING LUBIPROSTONE AND INTERMEDIATES THEREOF

(75) Inventors: Kiran Kumar Kothakonda, Bangalore (IN); Fan Wang, Hamilton (CA); Bhaskar Reddy Guntoori, Brantford (CA); Minh T. N. Nguyen, North York (CA); Alfredo Paul Ceccarelli, Brantford (CA); Yajun Zhao, Brantford (CA); Uma Kotipalli, Brantford (CA); Sammy Chris Duncan, Brantford (CA); Kaarina K. Milnes, London (CA); Kevin Wade Kells, Cambridge (CA); Laura Kaye Montemayor, St. George (CA)

(73) Assignee: Apotex Pharmachem Inc., Brantford, Ontario (CA)

( * ) Notice: Subject to any disclaimer, the term of this patent is extended or adjusted under 35 U.S.C. 154(b) by 1014 days.

(21) Appl. No.: 13/145,999

(22) PCT Filed: Jan. 22, 2010

(86) PCT No.: PCT/CA2010/000083
§ 371 (c)(1),
(2), (4) Date: Nov. 4, 2011

(87) PCT Pub. No.: WO2010/083597
PCT Pub. Date: Jul. 29, 2010

(65) Prior Publication Data
US 2012/0065409 A1    Mar. 15, 2012

Related U.S. Application Data

(60) Provisional application No. 61/146,483, filed on Jan. 22, 2009.

(51) Int. Cl.
| | | |
|---|---|---|
| C07D 323/04 | (2006.01) |
| C07D 311/00 | (2006.01) |
| C07D 315/00 | (2006.01) |
| C07D 307/93 | (2006.01) |
| C07C 61/06 | (2006.01) |
| C07C 69/74 | (2006.01) |
| C07F 7/18 | (2006.01) |
| C07C 69/734 | (2006.01) |
| C07C 69/738 | (2006.01) |
| C07C 405/00 | (2006.01) |
| C07D 307/935 | (2006.01) |

(52) U.S. Cl.
CPC .............. *C07F 7/1892* (2013.01); *C07C 69/734* (2013.01); *C07C 69/738* (2013.01); *C07C 405/00* (2013.01); *C07D 307/935* (2013.01); *C07C 2101/08* (2013.01)

(58) Field of Classification Search
CPC  C07C 2101/08; C07C 405/00; C07C 69/734; C07C 69/738; C07F 7/1892; C07D 307/935
USPC .................. 549/214, 396, 421, 465; 562/503; 560/121
See application file for complete search history.

(56) References Cited

U.S. PATENT DOCUMENTS

| | | |
|---|---|---|
| 5,117,042 A | 5/1992 | Ueno et al. |
| 5,229,529 A | 7/1993 | Ueno et al. |
| 5,284,858 A | 2/1994 | Ueno et al. |
| 5,468,880 A | 11/1995 | Ueno et al. |
| 6,414,016 B1 | 7/2002 | Ueno |
| 7,355,064 B2 | 4/2008 | Hirata et al. |
| 2007/0244333 A1 | 10/2007 | Hirata et al. |

FOREIGN PATENT DOCUMENTS

| | | |
|---|---|---|
| CA | 2639240 A1 | 2/2010 |
| CA | 2676759 A1 | 2/2010 |
| EP | 0503887 A2 | 9/1992 |

*Primary Examiner* — T. Victor Oh
(74) *Attorney, Agent, or Firm* — The Webb Law Firm

(57) ABSTRACT

There is provided processes for preparing Lubiprostone and intermediates thereof. Also provided are compounds, including intermediates for preparing Lubiprostone as well compositions comprising Lubiprostone and other compounds, including intermediates for preparing Lubiprostone and other compounds. (I)

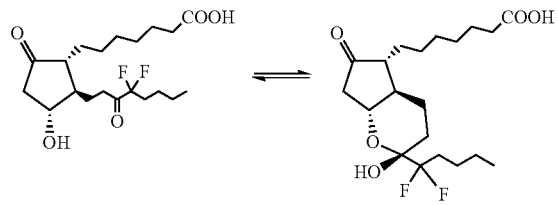

LUBIPROSTONE (1)

34 Claims, No Drawings

METHODS OF MAKING LUBIPROSTONE AND INTERMEDIATES THEREOF

TECHNICAL FIELD

This invention relates to the field of chemical synthesis of organic compounds and in particular to syntheses of Lubiprostone and intermediates thereof.

BACKGROUND

Lubiprostone (1) is an E1 type prostaglandin derivative. It is marketed in USA as Amitiza® and used for the treatment of idiopathic chronic constipation, irritable bowel syndrome and post operative ilues. The use of Lubiprostone softens the stool, increases motility, and promotes spontaneous bowel movements (SBM). Chemically, Lubiprostone is 7-[(2R,4aR,5R,7aR)-2-(1,1-difluoropentyl)-2-hydroxy-6-oxooctahydrocyclopenta[b]pyran-5-yl]heptanoic acid (*Drugs of the Future*, 2004, 29(4); 336-341):

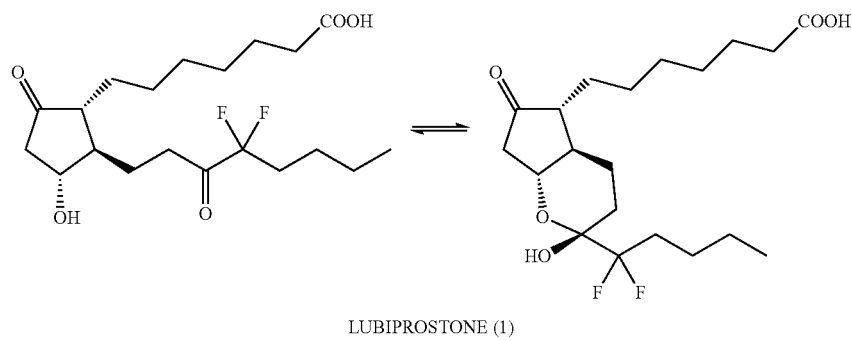 [SMILES: CCCCC(F)(F)C(=O)CC[C@H]1[C@H](O)CC(=O)[C@@H]1CCCCCCC(=O)O ; CCCCC(F)(F)[C@@]1(O)CC[C@H]2[C@@H](CC(=O)[C@@H]2CCCCCCC(=O)O)O1]

LUBIPROSTONE (1)

U.S. Pat. No. 5,117,042 discloses a method of treatment for improving encephalic function which comprises administering, to a subject in need of such treatment, a 15-keto-prostaglandin compound in an amount effective for improvement of encephalic function.

U.S. Pat. No. 5,284,858 teaches the novel 13,14-dihydro-15-keto prostaglandins E and use for treatment and prevention of several types of ulcers, such as duodenal ulcer and gastric ulcer.

U.S. Pat. No. 7,355,064 discloses an improved method for preparing 15-keto prostaglandin E derivative. According to U.S. Pat. No. 7,355,064, the deprotection of protected hydroxyl group required in manufacturing a 15-keto-prostaglandin derivative is conducted in the presence of a phosphoric acid compound.

US 2007244333 discloses a method for preparing a prostaglandin derivative of formula (A):

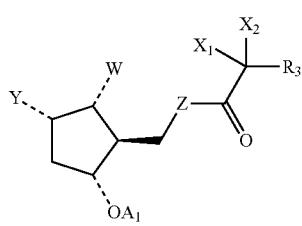

which comprises reacting an aldehyde represented by formula (B):

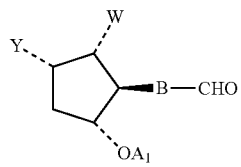

with a 2-oxoalkyl phosphonate in a reaction solvent under the presence of alkali hydroxide as sole base. By carrying out the reaction using an alkali hydroxide as sole base in the reaction system, the desired prostaglandin derivative can be obtained by simple procedures and with high yield.

U.S. Pat. No. 5,229,529 provides a method of preparing α,β-unsaturated ketolactones which are useful for production of prostaglandins having one or more halogen substituent(s) at the 16 or 17 position in high yield, in which, a dimethyl(2-oxoalkyl)phosphonate having one or more halogen substituents, a starting material, is reacted with a bicyclolactone aldehyde in the presence of an alkali metal hydride and a zinc compound.

U.S. Pat. No. 5,468,880 describes a method of producing α,β-unsaturated ketones by reacting aldehyde with 2-oxoalkyl phosphonate, wherein the reaction was carried out in the presence of a base and a zinc compound.

U.S. Pat. No. 6,414,016 provides an anti-constipation composition containing a halogenated-bi-cyclic compound as an active ingredient in a ratio of bicyclic/monocyclic structure of at least 1:1.

SUMMARY

The present invention is directed to methods of preparation of Lubiprostone, various intermediates useful in the preparation of Lubiprostone and methods of preparation of such intermediates.

This invention is based, at least in part, on providing a suitable protecting group, which protecting group comprises $R^1$, $R^2$ and $R^3$ together with the carbon to which each one of $R^1$, $R^2$ and $R^3$ are attached on a compound of Formula 6 in Scheme 1. A suitable protecting group is any protecting group that may be removed using hydrogen. Specific, non-limiting examples of suitable protecting groups are provided herein. A compound of Formula 6 may be used as an intermediate in a synthetic route to Lubiprostone whereby several transformations including reduction of two double bonds and deprotection of two groups may be consolidated into one step.

In illustrative embodiments of the present invention, Lubiprostone and the intermediates thereof may be prepared by an exemplary process as set out in Scheme 1. Exemplary reagents and conditions for these reactions are disclosed herein.

SCHEME 1
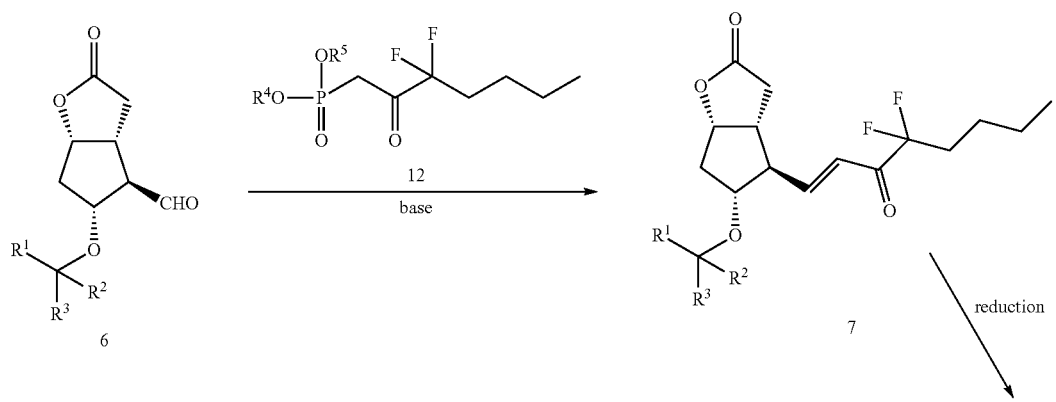
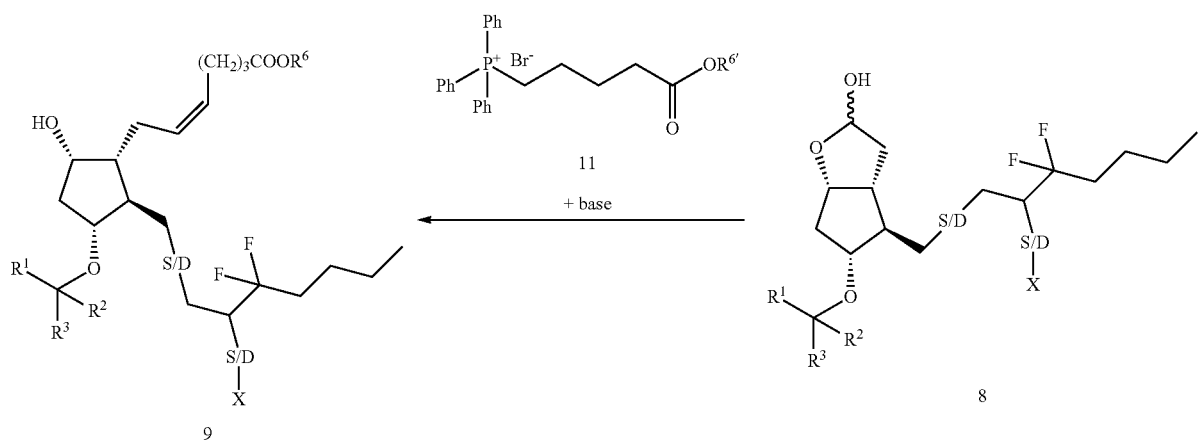
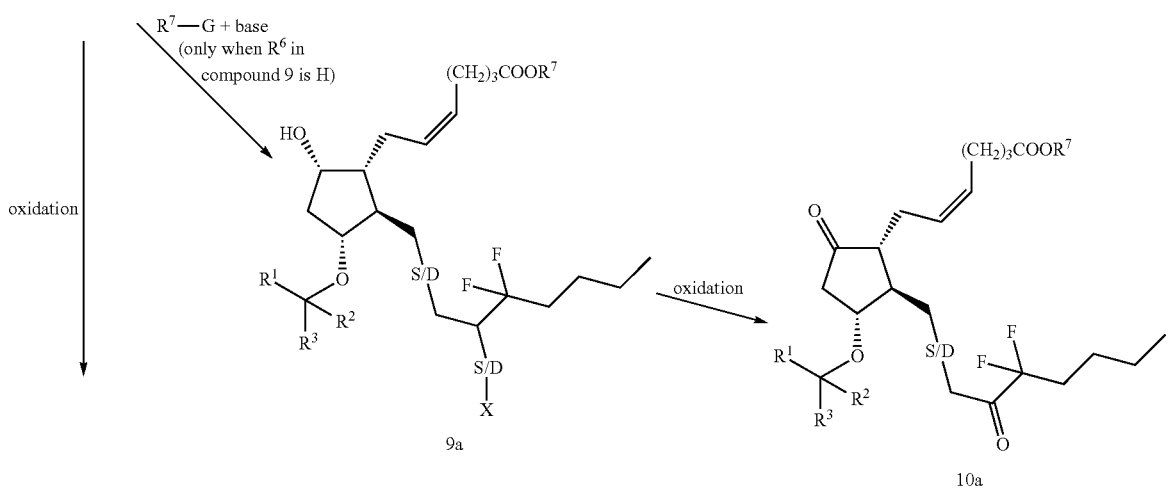

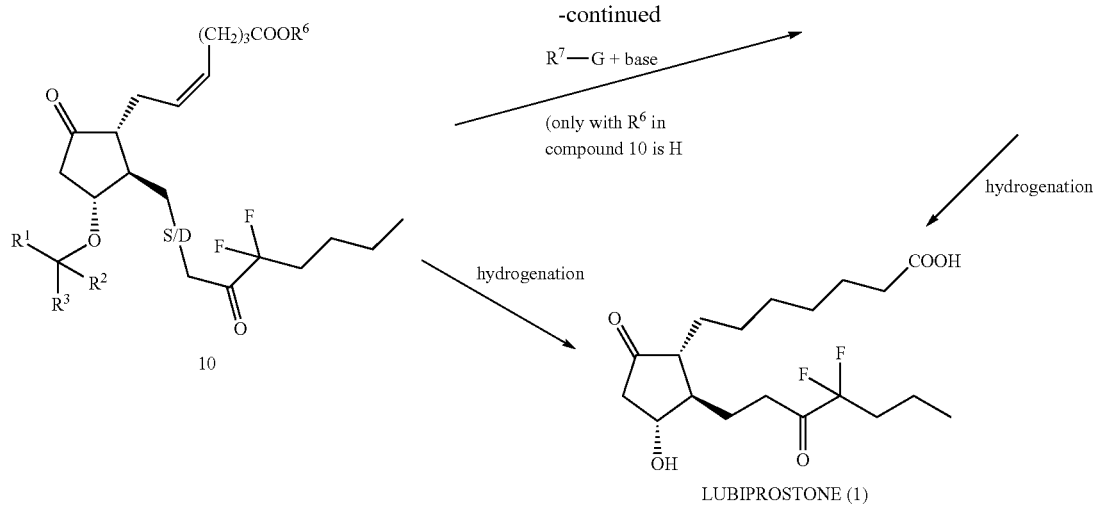

In Scheme 1 above, $R^1$, $R^2$ and $R^3$ independently selected from the group consisting of H, alkyl, substituted alkyl, aryl, substituted aryl, arylalkyl, and substituted arylalkyl; wherein at least one of $R^1$, $R^2$ and $R^3$ is aryl or substituted aryl;

$R^4$ and $R^5$ are independently a short chain alkyl;

$R^6$ and $R^{6'}$ are independently H or $R^7$;

$R^7$ is $C(R^{1'})(R^{2'})(R^{3'})$, where $R^{1'}$, $R^{2'}$ and $R^{3'}$ may be as defined herein for $R^1$, $R^2$ and $R^3$, respectively;

X is OH or O;

G is a leaving group; and

"S/D" bonds may be single or double bonds.

In illustrative embodiments of the present invention, Lubiprostone and the intermediates thereof may be prepared by an exemplary process as set out in Scheme 2. Exemplary reagents and conditions for these reactions are disclosed herein.

SCHEME 2

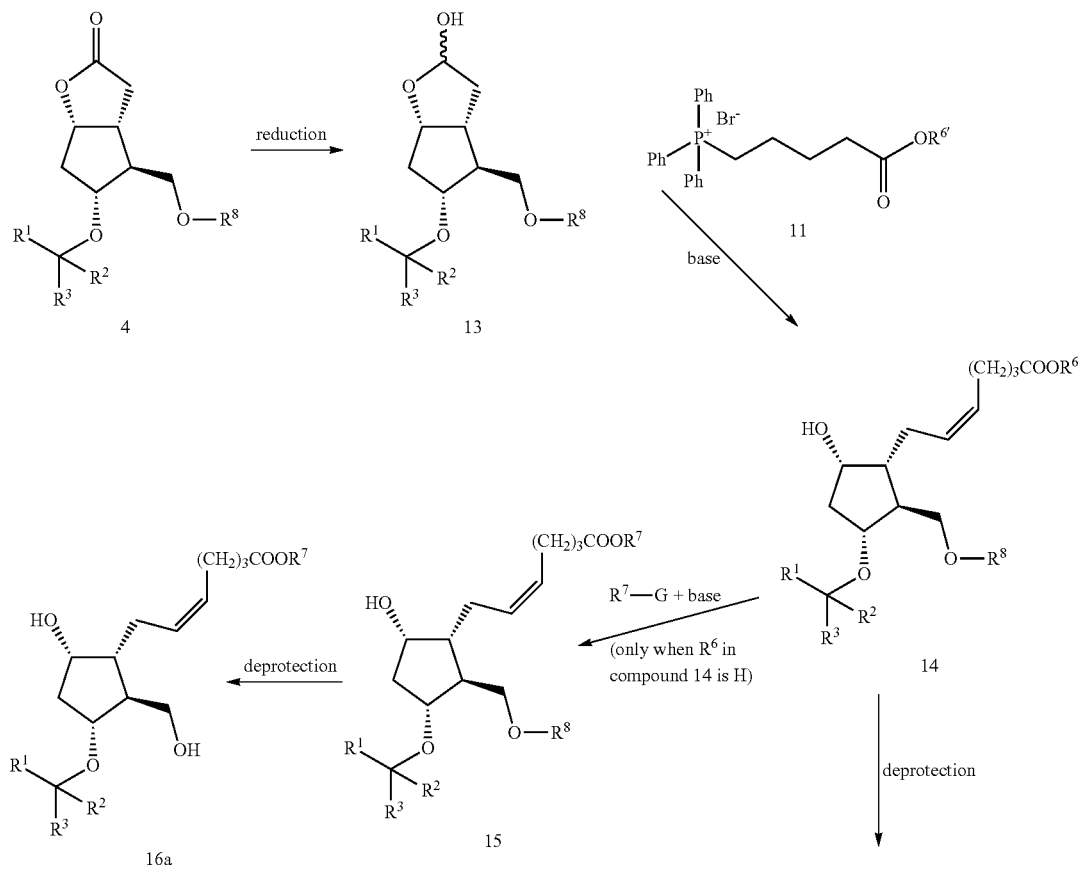

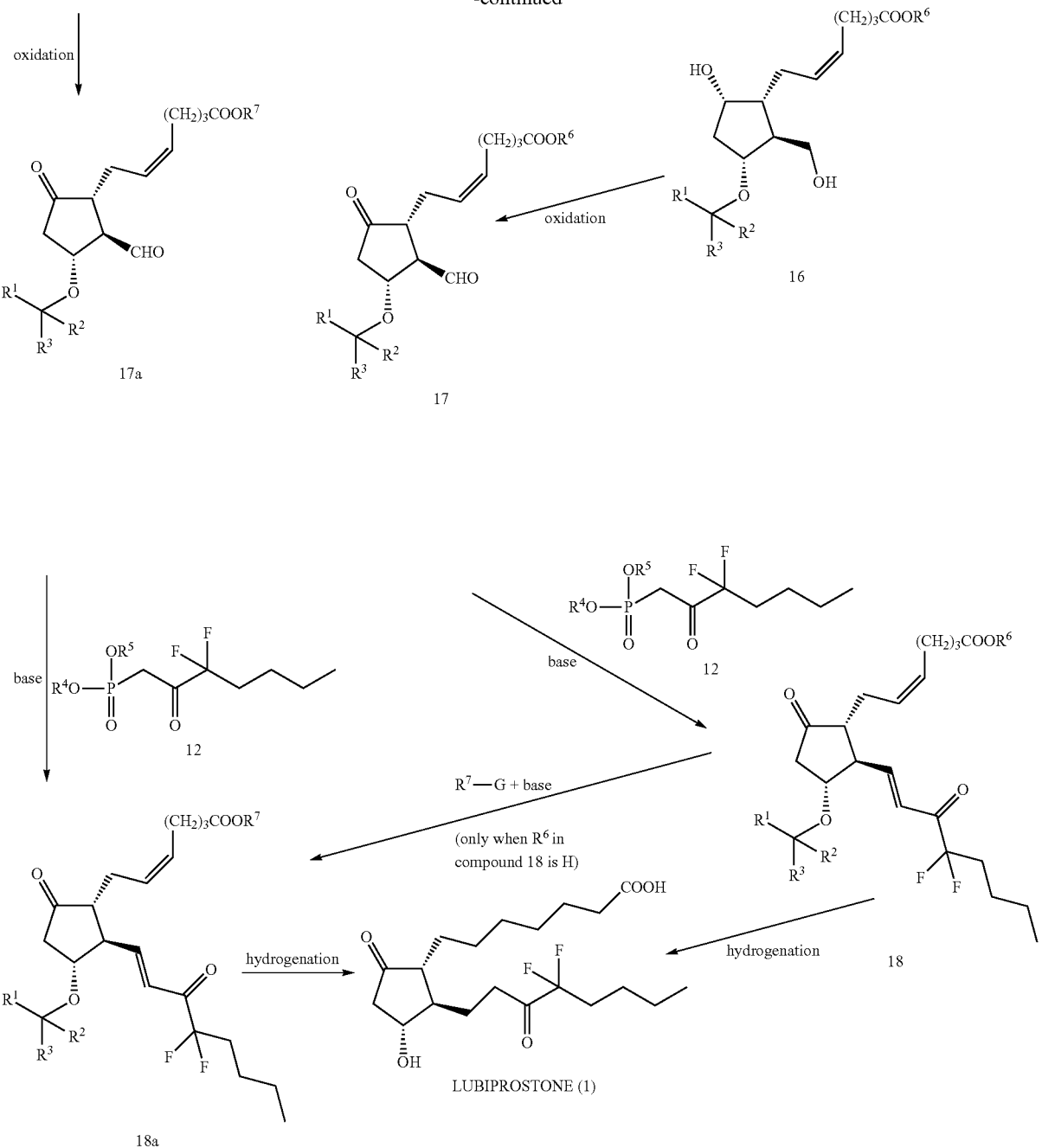

In Scheme 2 above, $R^1$, $R^2$ and $R^3$ are independently selected from the group consisting of H, alkyl, substituted alkyl, aryl, substituted aryl, arylalkyl, and substituted arylalkyl; wherein at least one of $R^1$, $R^2$ and $R^3$ is aryl or substituted aryl;

$R^4$ and $R^5$ are independently a short chain alkyl;

$R^6$ and $R^{6'}$ are independently H or $R^7$;

$R^7$ is $C(R^{1'})(R^{2'})(R^{3'})$, where $R^{1'}$, $R^{2'}$ and $R^{3'}$ may be as defined herein for $R^1$, $R^2$ and $R^3$, respectively;

$R^8$ is a silyl protecting group; and

G is a leaving group.

In illustrative embodiments of the present invention, Lubiprostone and the intermediates thereof may be prepared by an exemplary process as set out in Scheme 3. Exemplary reagents and conditions for these reactions are disclosed herein.

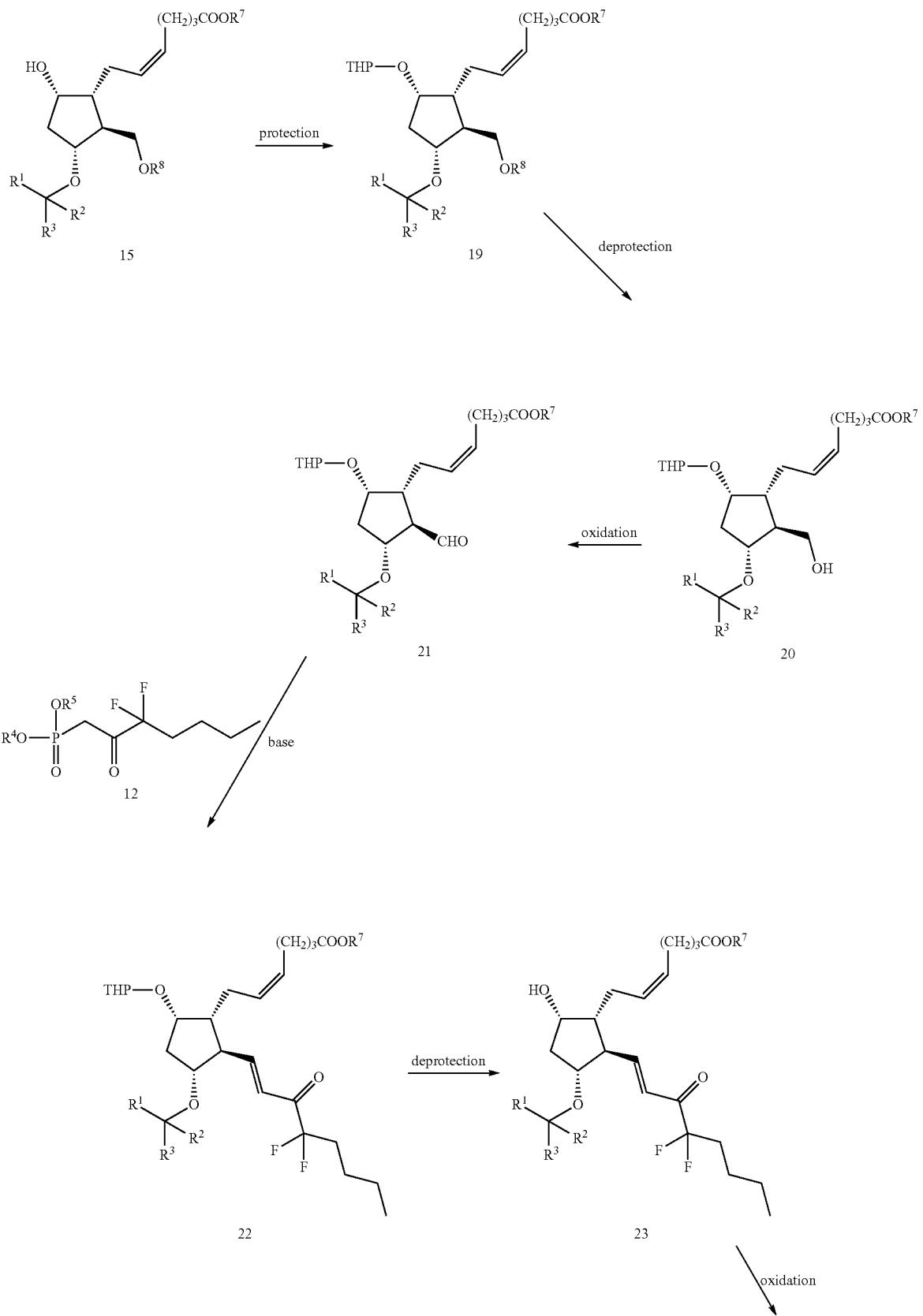

-continued

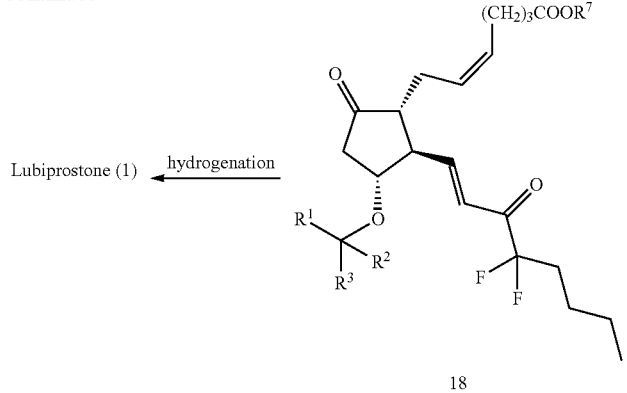

In Scheme 3 above compound 15 may be a compound of Formula 14 wherein $R^6$ is $R^7$;

$R^1$, $R^2$ and $R^3$ are independently selected from the group consisting of H, alkyl, substituted alkyl, aryl, substituted aryl, arylalkyl, and substituted arylalkyl; wherein at least one of $R^1$, $R^2$ and $R^3$ is aryl or substituted aryl;

$R^4$ and $R^5$ are independently a short chain alkyl;

$R^7$ is $C(R^{1'})(R^{2'})(R^{3'})$, where $R^{1'}$, $R^{2'}$ and $R^{3'}$ may be as defined for $R^1$, $R^2$ and $R^3$, respectively;

$R^8$ is a silyl protecting group; and

THP is tetrahydropyranyl.

In illustrative embodiments of the present invention, there is provided a process for preparation of Lubiprostone comprising: reacting in the presence of a first base, a compound of Formula 6

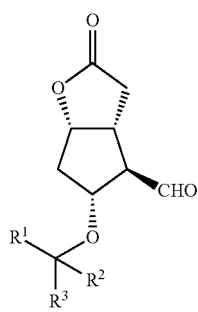

with a 2-oxoalkyl phosphonate of Formula 12

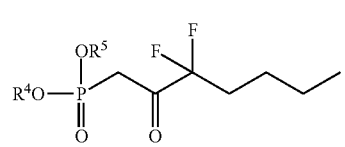

thereby forming a compound of Formula 7

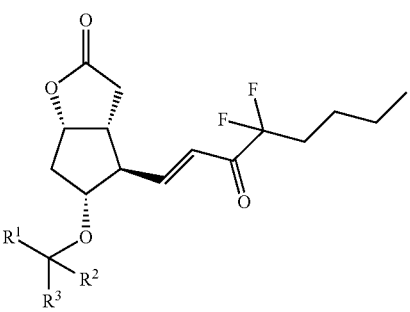

reducing, using a reducing agent, the compound of Formula 7 to a compound of Formula 8

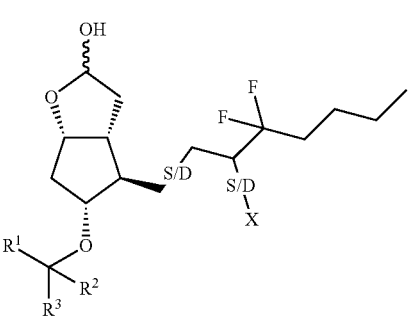

reacting, in the presence of a second base, the compound of Formula 8 with a compound of Formula 11

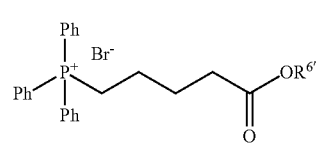

thereby forming a compound of Formula 9:

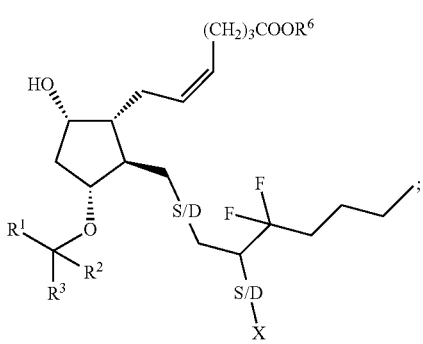

oxidizing the compound of Formula 9 thereby forming the compound of Formula 10

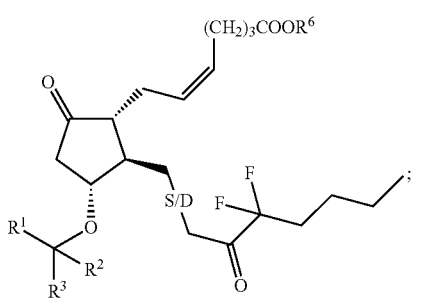

hydrogenation, in the presence of a catalyst, of the compound of Formula 10 to Lubiprostone, wherein $R^1$, $R^2$ and $R^3$ are independently selected from the group consisting of H, alkyl, substituted alkyl, aryl, substituted aryl, arylalkyl, and substituted arylalkyl; wherein at least one of $R^1$, $R^2$ and $R^3$ is aryl or substituted aryl; $R^4$ and $R^5$ are independently a short chain alkyl; $R^6$ and $R^{6'}$ are independently H or $R^7$; $R^7$ is $C(R^{1'})(R^{2'})(R^{3'})$, where $R^{1'}$, $R^{2'}$ and $R^{3'}$ may be as defined herein for $R^1$, $R^2$ and $R^3$, respectively; X is OH or O; each S/D is independently a single or a double bond.

In illustrative embodiments of the present invention, there is provided a process for preparation of a compound of Formula 6:

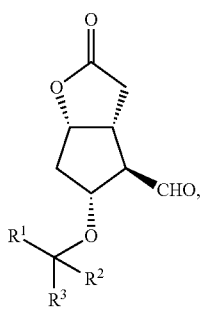

the process comprising: i) reacting a compound of Formula 2:

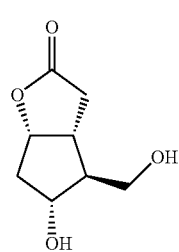

with $R^8$-G, wherein $R^8$ is a silyl protecting group and G is a leaving group, thereby forming a compound of Formula 3:

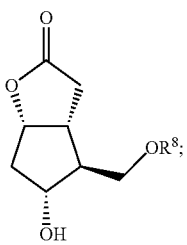

ii) reacting the compound of Formula 3 with a compound having the structure:

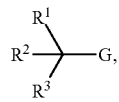

thereby forming a compound of Formula 4:

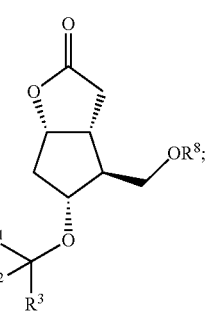

iii) reacting the compound of Formula 4 with tetra-n-butylammonium fluoride (TBAF), thereby forming a compound of Formula 5:

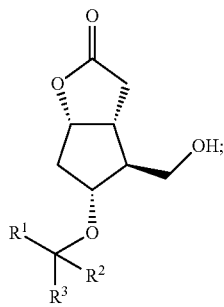

and iv) oxidizing the compound of Formula 5 thereby forming the compound of Formula 6, wherein $R^1$, $R^2$ and $R^3$ are independently selected from the group consisting of H, alkyl, substituted alkyl, aryl, substituted aryl, arylalkyl, and substituted arylalkyl; wherein at least one of $R^1$, $R^2$ and $R^3$ is aryl or substituted aryl.

In illustrative embodiments of the invention there is provided intermediate compounds and starting material compounds as set out in herein.

Other aspects and features of the present invention will become apparent to those ordinarily skilled in the art upon review of the following description of specific embodiments of the invention in conjunction with the accompanying figures.

DETAILED DESCRIPTION

In chemical structures depicted herein, bonds labeled "S/D" may be single or double bonds. Depending on whether or not the "S/D" bond is a single or double bond, the number of hydrogen atoms bonded to atoms connected by the "S/D" bond will be sufficient to provide for normal valency of the atoms connected by the "S/D" bond. For example if two carbon atoms are depicted as being connected by an "S/D" bond, then if they are connected by a single bond, each carbon atom will have 4-q hydrogen atoms bonded to it where q is the number of bonds from the carbon atom to non-hydrogen atoms (including the "S/D" bond). Similarly if two carbon atoms are connected by a double bond, then each carbon atom will have 3-q hydrogen atoms bonded to it. Another example is if an oxygen atom is depicted as being connected to a carbon atom by an "S/D" bond, then the oxygen atom will have 2-q hydrogen atoms if the "S/D" bond is a single bond and will have 1-q hydrogen atoms if the "S/D" bond is a double bond.

As used herein, the term "substituted" refers to the replacement of a hydrogen atom on a compound with a substituent group. A substituent may be a non-hydrogen atom or multiple atoms of which at least one is a non-hydrogen atom and one or more may or may not be hydrogen atoms. For example, without limitation, substituted compounds may comprise one or more substituents selected from the group consisting of: R", OR", NR"R"', SR", halogen, SiR"R"'R"", OC(O)R", C(O)R", CO$_2$R", CONR"R"', NR"'C(O)$_2$R", S(O)R", S(O)$_2$R", CN and NO$_2$.

As used herein, each R", R"', and R"" may be selected, independently, from the group consisting of: hydrogen, halogen, oxygen, substituted or unsubstituted heteroalkyl, substituted or unsubstituted aryl, substituted or unsubstituted alkyl, alkoxy or thioalkoxy groups, and arylalkyl groups.

As used herein, the term "alkyl" by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (e.g. $C_1$-$C_{10}$ or 1- to 10-membered means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "lower alkyl" comprises straight chain or branched chain saturated hydrocarbon groups having 1 to 4 carbon atoms, for instance, methyl, ethyl, propyl, isopropyl, butyl, isobutyl, sec-butyl, and t-butyl. Lower alkyls may be substituted or unsubstituted.

The term "short chain alkyl" means an alkyl group having 1 to 3 carbon atoms. Short chain alkyls may be substituted or unsubstituted.

As used herein, the term "aryl" by itself or as part of another substituent, means, unless otherwise stated, a polyunsaturated, aromatic, hydrocarbon substituent which can be a single ring or multiple rings (often from 1 to 3 rings) which are fused together or linked covalently. "Aryl" includes, but is not limited to, "heteroaryl" groups. "Heteroaryl" refers to an aryl group that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include: phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridinyl, 3-pyridinyl, 4-pyridinyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. The term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, etc.) including those alkyl groups in which a carbon atom containing group (e.g., a methylene group) has been replaced by, for example, an oxygen atom (e.g., phenoxymethyl, 2-pyridyloxymethyl, 3-(1-naphthyloxy)propyl, etc).

As used herein the term "leaving group" refers to a halogen atom (e.g. chlorine, bromine and iodine) and/or sulfonyloxy groups (e.g. methanesulfonyloxy, trifluoromethanesulfonyloxy, p-toluenesulfonyloxy).

The term "hydrogenation" means a chemical reaction that results in addition of two hydrogen atoms. As such, it is meant to include both addition of hydrogen to saturate an unsaturated bond as well as addition of hydrogen to a single bond to cause bond breakage (hydrogenolysis) as well as other reactions involving the addition of two hydrogen atoms.

Some atoms herein are referred to by a number. The number may be assigned to the atom using one of a number of different conventions. In some cases, standard nomenclature, such as IUPAC nomenclature, is used to associate a number with a particular atom in a structure. Such numbering may be found in the names of compounds which are set out herein. As used herein, when referring to the location the bonds that may be single or double bonds, the following numbering conventions may also be used:

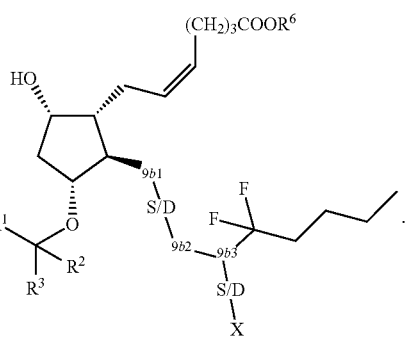

9

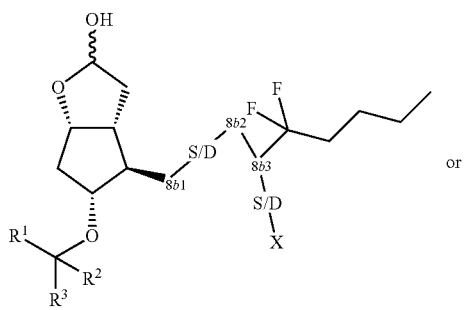

8 or

In general, when referring to the location of a bond that may be a single bond or a double bond, if the numbered atom being referred to herein is part of a compound containing a bicyclic structure similar to Formula 8 above, then the numbering convention associated with Formula 8 above will be used. If the numbered atom being referred to herein is part of a compound containing a mono-cyclic structure similar to Formula 9 above, then the numbering convention associated with Formula 9 above will be used. For example, referring to Formula 8 above, there is an S/D bond between carbon 8b1 and carbon 8b2 as well as an S/D bond between carbon 8b3 and group X. Similarly, referring to Formula 9, there is an S/D bond between carbon 9b1 and carbon 9b2 as well as an S/D bond between carbon 9b3 and group X. Such atom numbering is not related to and is not reflected in the numbering of atoms associated with the nomenclature of compounds herein.

According to illustrative embodiments of the present invention, Lubiprostone may be prepared according to Scheme 1 starting from a compound of Formula 6.

SCHEME 1

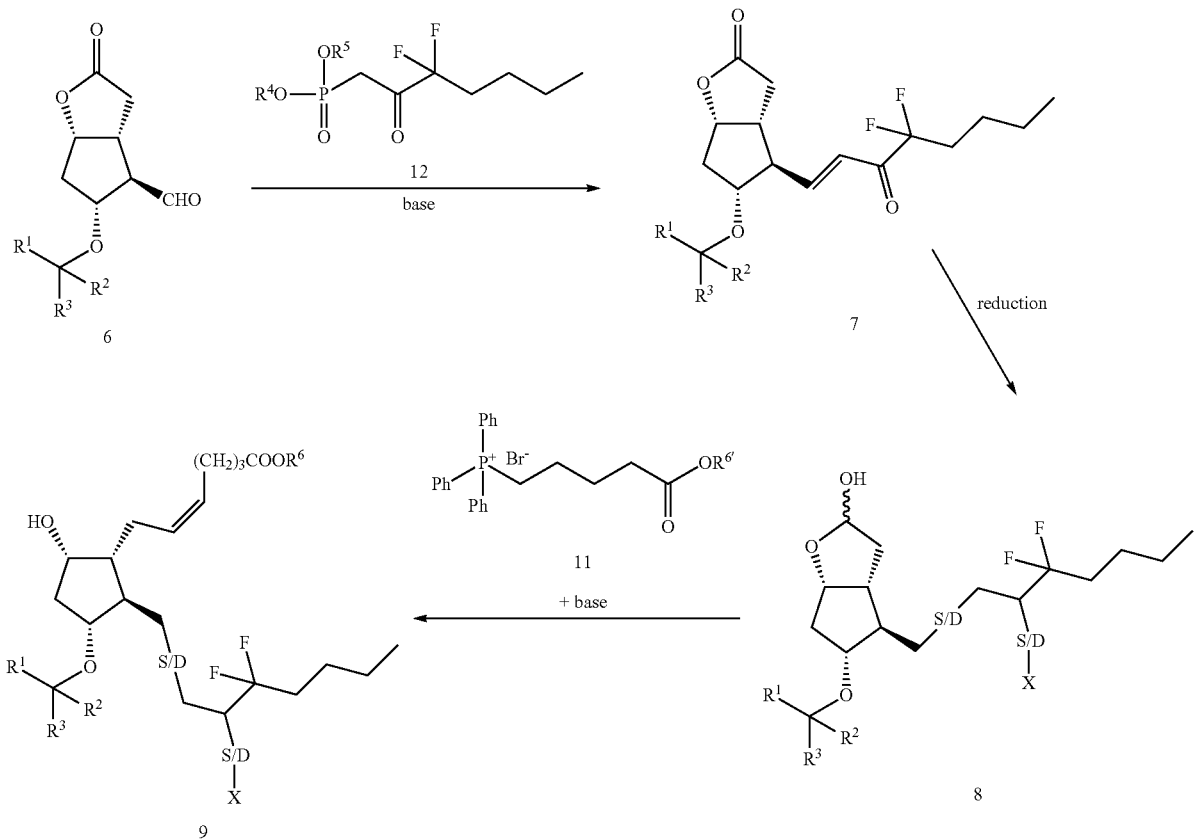

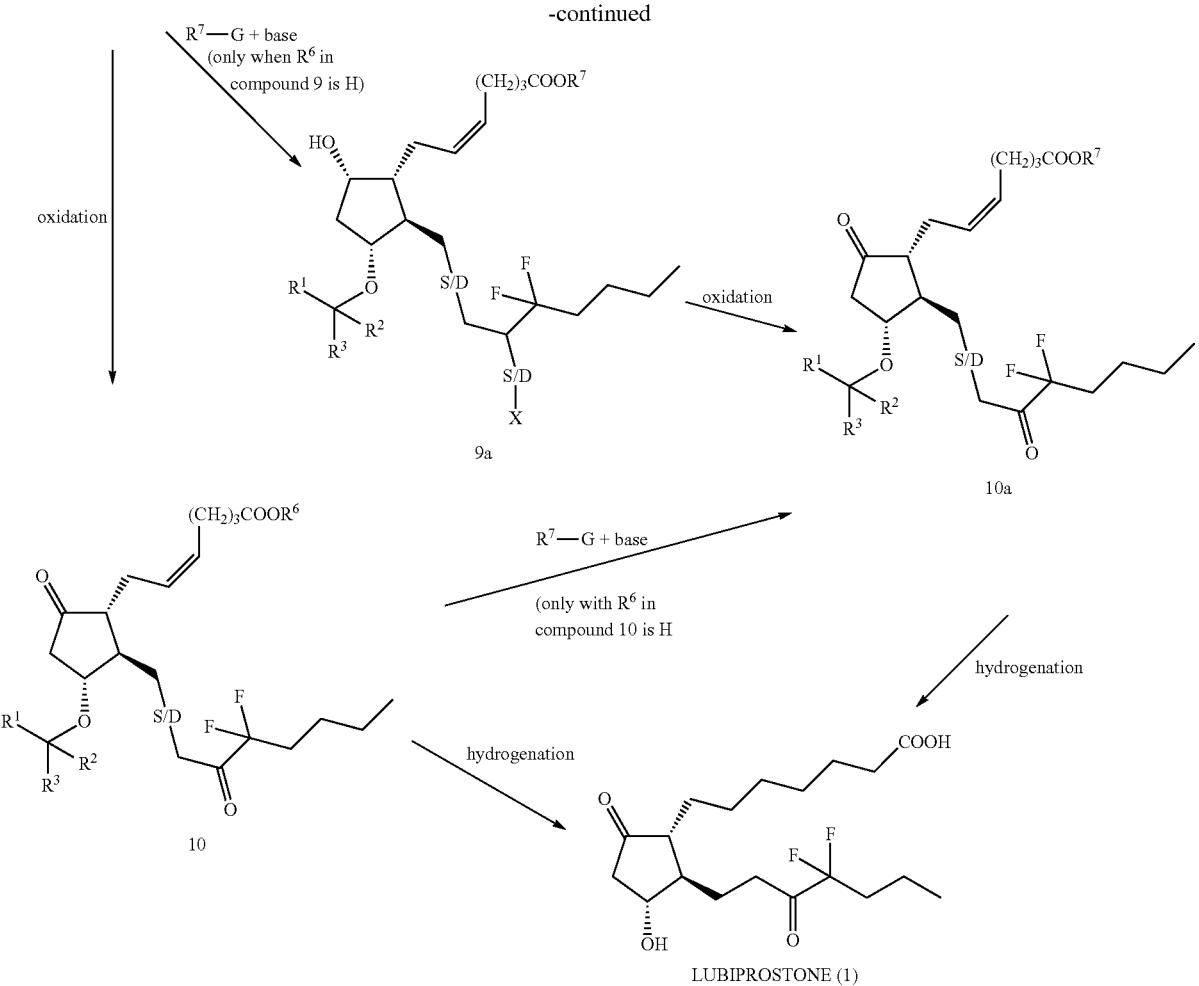

In Scheme 1 above, $R^1$, $R^2$ and $R^3$ independently selected from the group consisting of H, alkyl, substituted alkyl, aryl, substituted aryl, arylalkyl, and substituted arylalkyl; wherein at least one of $R^1$, $R^2$ and $R^3$ is aryl or substituted aryl;

$R^4$ and $R^5$ are independently a short chain alkyl;

$R^6$ and $R^{6'}$ are independently H or $R^7$;

$R^7$ is $C(R^{1'})(R^{2'})(R^{3'})$, where $R^{1'}$, $R^{2'}$ and $R^{3'}$ may be as defined herein for $R^1$, $R^2$ and $R^3$, respectively;

X is OH or O;

G is a leaving group; and

"S/D" bonds may be single or double bonds.

A compound of Formula 6 may be prepared from a commercially available lactone according to the route shown in Scheme 4.

Scheme 4

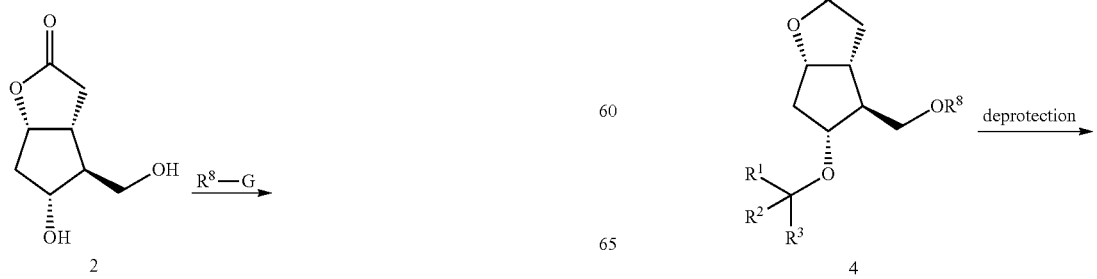

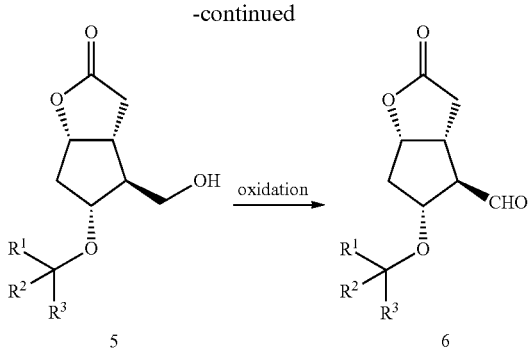

In Scheme 4 above, $R^1$, $R^2$ and $R^3$ are independently selected from the group consisting of H, alkyl, substituted alkyl, aryl, substituted aryl, arylalkyl, and substituted arylalkyl; wherein at least one of $R^1$, $R^2$ and $R^3$ is aryl or substituted aryl;

$R^8$ is a silyl protecting group; and

G is a leaving group.

In some embodiments of Formulas 4, 5 and 6, each of $R^1$, $R^2$ and $R^3$ are independently an aryl or substituted aryl. In some embodiments of Formulas 4, 5 and 6, each of $R^1$, $R^2$ and $R^3$ are three separate aryl or substituted aryl moieties in which each aryl or substituted aryl moiety is the same functional group (e.g. each of $R^1$, $R^2$ and $R^3$ are independently a phenyl group). In other embodiments, two of the moieties of $R^1$, $R^2$ and $R^3$ are the same functional group and the other is a different functional group. In other embodiments each of $R^1$, $R^2$ and $R^3$ are all different. In some embodiments, only one of $R^1$, $R^2$ and $R^3$ is hydrogen. In some embodiments, only two of $R^1$, $R^2$ and $R^3$ are hydrogen. In some embodiments of Formulas 4, 5 and 6, one of $R^1$, $R^2$ and $R^3$ is aryl or substituted aryl and the other two are hydrogen. In some embodiments of Formulas 4, 5 and 6, one of $R^1$, $R^2$ and $R^3$ is aryl and the other two are hydrogen. In some embodiments of Formulas 4, 5 and 6, at least one of $R^1$, $R^2$ and $R^3$ is phenyl. In some embodiments of Formulas 4, 5 and 6, $R^1$, $R^2$, and $R^3$, when taken together and with the carbon atom to which they are bonded, provide a moiety selected from the group consisting of: 2-phenyl-2-propyl, triphenylmethyl, diphenylmethyl, and (p)-methoxyphenyldiphenylmethyl. In some embodiments of Formulas 4, 5 and 6, at least one of $R^1$, $R^2$ and $R^3$ is substituted phenyl. In some embodiments of Formulas 4, 5 and 6, at least one of $R^1$, $R^2$ and $R^3$ is phenyl substituted with one or more substituents selected from the group consisting of: methoxy, nitro, phenyl, chloro, trifluoromethyl and C1-C6 alkyl. In some embodiments of Formulas 4, 5 and 6, at least one of $R^1$, $R^2$ and $R^3$ is phenyl substituted with one or more substituents selected from the group consisting of: (4)-methoxy; (3,4)-dimethoxy; (2,6)-dimethoxy; (2)-nitro; (4)-nitro; (4)-phenyl; (2,6)-dichloro; (2)-trifluoromethyl; (4)-trifluoromethyl; (2,4)-dimethyl and (4)-methyl. In some embodiments of Formulas 4, 5 and 6, one of $R^1$, $R^2$ and $R^3$ is phenyl or substituted phenyl and the other two are hydrogen. In some embodiments of Formulas 4, 5 and 6, one of $R^1$, $R^2$ and $R^3$ is phenyl and the other two are hydrogen.

According to illustrative embodiments of the present invention, a process for preparation of a compound of Formula 6 is provided comprising the steps as shown in Scheme 4 Each G may be independently selected from the group consisting of: halogen atoms (e.g. chlorine, bromine and iodine) and sulfonyloxy groups (e.g. methanesulfonyloxy, trifluoromethanesulfonyloxy, p-toluenesulfonyloxy). In some embodiments, each G may be independently selected from the group consisting of: chlorine, bromine, iodine, methanesulfonyloxy, trifluoromethanesulfonyloxy, p-toluenesulfonyloxy. In some embodiments, each G may be independently selected from the group consisting of: chlorine and bromine. In some embodiments $R^8$ is triisopropylsilyl (TIPS). The deprotection of the compound of Formula 4 may comprise using TBAF. Oxidation may occur in the presence of an oxidizing agent. The oxidizing agent may be selected from the group consisting of Dess-Martin periodinane, IBX, $CrO_3$, $MnO_2$, TEMPO/sodium hypochlorite and $SO_3$/pyridine. The oxidation may occur by way of a Swern oxidation or a Corey-Kim oxidation. The oxidizing agent may be $SO_3$/pyridine.

According to illustrative embodiments of the present invention a process for preparation of Lubiprostone is provided comprising hydrogenation, in the presence of a suitable hydrogenation catalyst, of a compound of Formula 10 or Formula 10a:

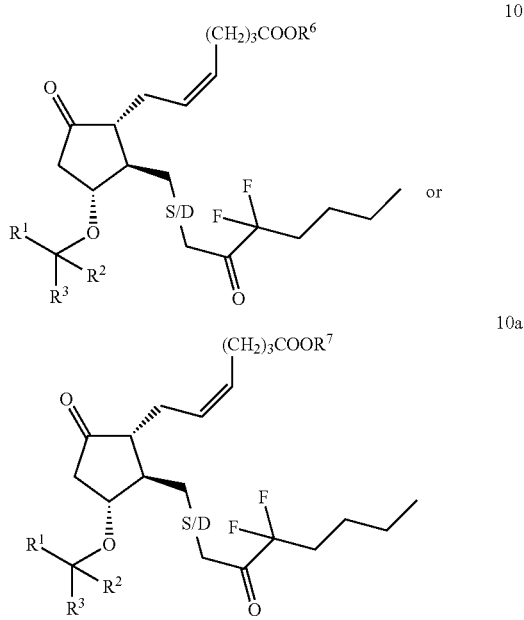

wherein:

$R^1$, $R^2$ and $R^3$ may be as defined above for any of Formulas 4, 5 and/or 6;

$R^6$ is H or $R^7$;

$R^7$ is $C(R^{1'})(R^{2'})(R^{3'})$, where $R^{1'}$, $R^{2'}$ and $R^{3'}$ may be as defined herein for $R^1$, $R^2$ and $R^3$, respectively; and "S/D" bonds may be single or double bonds.

In some embodiments of Formula 10, $R^6$ is H.

In some embodiments of Formula 10, $R^6$ is $R^7$. In some embodiments of Formula 10 and/or Formula 10a, $R^7$ is an arylalkyl or a substituted arylalkyl of the formula, $C(R^{1'})(R^{2'})(R^{3'})$ wherein $R^{1'}$, $R^{2'}$ and $R^{3'}$ may be as defined herein for $R^1$, $R^2$ and $R^3$. In some embodiments of Formula 10 and/or Formula 10a, $R^7$ is benzyl. In some embodiments of Formulas 10 and/or 10a $R^7$ is selected from the group consisting of: 2-phenyl-2-propyl, triphenylmethyl, diphenylmethyl, and (p)-methoxyphenyldiphenylmethyl. In some embodiments of Formula 10 and/or Formula 10a, $R^7$ is benzyl substituted with one or more substituents selected from the group consisting of: methoxy, nitro, phenyl, chloro, trifluoromethyl and C1-C6 alkyl. In some embodiments of Formula 10 and/or Formula 10a, $R^7$ is benzyl substituted with one or more substituents selected from the group consisting of: (4)-methoxy; (3,4)-dimethoxy; (2,6)-dimethoxy; (2)-nitro; (4)-nitro; (4)-phenyl; (2,6)-dichloro; (2)-trifluoromethyl; (4)-trifluoromethyl; (2,4)-dimethyl and (4)-methyl.

In some embodiments of Formula 10 and/or Formula 10a, S/D is a single bond. In some embodiments of Formula 10 and/or Formula 10a, S/D is a double bond. Some embodiments of Formula 10 and/or Formula 10a comprise a mixture of compounds in which a portion of the mixture of compounds comprise a single bond at the S/D bond and another portion of the mixture of compounds comprises a double bond at the S/D bond.

The suitable hydrogenation catalyst may be selected from the group consisting of palladium, platinum, rhodium, ruthenium, and Raney-nickel. The suitable hydrogenation catalyst may be finely dispersed solids or adsorbed on an inert support such as carbon or alumina. The suitable hydrogenation catalyst may be wet or dry. The suitable hydrogenation catalyst may be 10 wt % palladium on carbon (dry basis), 50 wt % (wet support). The catalyst loading may be from about 0.1 wt % to about 10 wt % palladium with respect to the weight of a compound of Formula 10 and/or Formula 10a. The catalyst loading may be from about 0.1 wt % to about 3 wt % palladium with respect to the weight of a compound of Formula 10 and/or Formula 10a. The catalyst loading may be about 1 wt % palladium with respect to the weight of a compound of Formula 10 and/or Formula 10a. The hydrogenation may be performed by using hydrogen gas or transfer hydrogenation.

Hydrogenation may be carried out in the presence of a fifth solvent. The fifth solvent may be ethyl acetate, methanol, ethanol, methyl t-butyl ether (MTBE), or mixtures thereof. Often, the fifth solvent is ethyl acetate.

According to illustrative embodiments of the present invention, there is provided a process described herein whereby the compound of Formula 10 is prepared by oxidation of a compound of Formula 9:

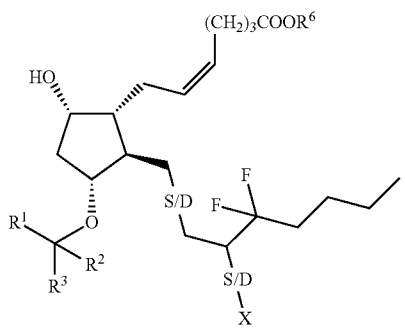

9 wherein
$R^1$, $R^2$, and $R^3$ may be as defined above for any of Formulas 4, 5, 6, 10 and/or 10a;
$R^6$ is H or $R^7$;
$R^7$ may be as defined above for any of Formulas 10 and/or 10a;
X is H or OH; and
"S/D" bonds may be single or double bonds.

Oxidation may occur by way of a Swern oxidation. Oxidation may occur in the presence of an oxidizing agent. The oxidizing agent may be selected from the group consisting of Dess-Martin periodinane, IBX, $CrO_3$, $MnO_2$, TEMPO/sodium hypochlorite and $SO_3$/pyridine. The oxidizing agent may be Dess-Martin periodinane. The oxidizing agent may be $SO_3$/pyridine.

Oxidation may occur in the presence of a fourth solvent. The fourth solvent may be dichloromethane, dimethylsulfoxide (DMSO), or mixtures thereof. Often, the fourth solvent is dichloromethane.

In some embodiments of Formula 9, the S/D bond between the carbon at position 9b1 and 9b2 is a single bond. In some embodiments of Formula 9, S/D bond between the carbon at position 9b1 and 9b2 is a double bond. Some embodiments Formula 9 comprise a mixture of compounds in which a portion of the mixture of compounds comprise a single bond between the carbon at position 9b1 and the carbon at position 9b2 and another portion of the mixture of compounds comprise a double bond between the carbon at position 9b1 and the carbon at position 9b2. In some embodiments of Formula 9, the S/D bond between the carbon at position 9b3 and group X is a single bond. In some embodiments of Formula 9, the S/D bond between the carbon at position 9b3 and group X is a double bond. Some embodiments Formula 9 comprise a mixture of compounds in which a portion of the mixture of compounds comprise a single bond between the carbon at position 9b3 and group X and another portion of the mixture of compounds comprise a double bond between the carbon at position 9b3 and group X. Some embodiments of Formula 9 comprise a mixture of two or more compounds selected from the group consisting of:

a) compounds comprising i) a single bond between the carbon at position 9b1 and the carbon at position 9b2 and ii) a single bond between the carbon at position 9b3 and group X;

b) compounds comprising i) a single bond between the carbon at position 9b1 and the carbon at position 9b2 and ii) a double bond between the carbon at position 9b3 and group X;

c) compounds comprising i) a double bond between the carbon at position 9b1 and the carbon at position 9b2 and ii) a single bond between the carbon at position 9b3 and group X; and d) compounds comprising i) a double bond between the carbon at position 9b1 and the carbon at position 9b2 and ii) a double bond between the carbon at position 9b3 and group X.

A subset of the compounds of Formula 9 is compounds of Formula 9a:

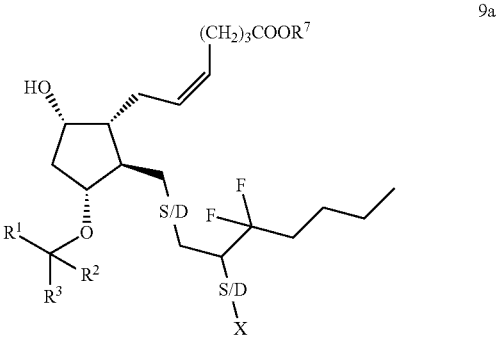

9a wherein
$R^1$, $R^2$, $R^3$ and $R^7$ may be as defined above for any of Formulas 4, 5, 6, 9, 10 and/or 10a;
X is O or OH; and
"S/D" bonds may be single or double bonds as defined above for Formula 9.

More specifically, when $R^6$ in Formula 9 is $R^7$, such compounds are also compounds of Formula 9a. Similarly, compounds of Formula 10a are a subset of compounds of Formula 10. Compounds of Formula 10a may be prepared by oxidation of compounds of Formula 9a in the same or a similar manner as described above for preparing compounds of Formula 10 from compounds of Formula 9.

It is possible to prepare embodiments of Formula 10a as described above for Formula 10. Alternatively, a compound of Formula 10a may be prepared from a compound of Formula 10 wherein $R^6$ is H by reacting the compound of Formula 10 wherein $R^6$ is H with $R^7$-G, wherein $R^7$ may be as defined above for one of Formulas 9, 9a and/or 10 and G is a leaving group. G may be selected from the group consisting of: halogen atoms (e.g. chlorine, bromine and iodine) and sulfonyloxy groups (e.g. methanesulfonyloxy, trifluoromethanesulfonyloxy, p-toluenesulfonyloxy). In some embodiments, G may be selected from the group consisting of: chlorine, bromine, iodine, methanesulfonyloxy, trifluoromethanesulfonyloxy, and p-toluenesulfonyloxy. In some embodiments, G may be selected from the group consisting of: bromine. The compound of Formula $R^7$-G may be a benzyl halide whereby the benzyl is substituted or unsubstituted. The compound of Formula $R^7$-G may be benzyl bromide. The reaction of $R^7$-G with the compound of Formula 10 wherein $R^6$ is H may be conducted in the presence of a fourth base. The fourth base may be organic or inorganic. The fourth base may be selected from the group consisting of triethylamine, diisopropylamine, diisopropylethylamine, pyridine and 1,8-diazabicyclo[5.4.0]undec-7-ene (DBU). The fourth base may be diisopropylamine. The fourth base may be pyridine.

According to illustrative embodiments of the present invention a compound of Formula 9 (including compounds of Formula 9a) may be prepared by reacting, in the presence of a second base, a compound of Formula 8:

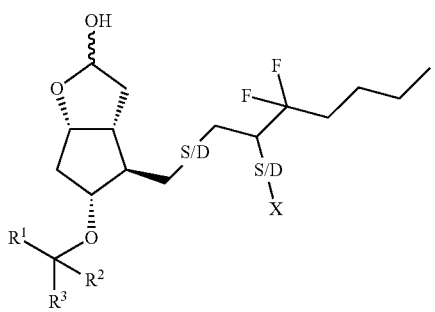

8 wherein
$R^1$, $R^2$, $R^3$, and X may be as defined above for any of Formulas 4, 5, 6, 9, 9a, 10 and/or 10a;
and "S/D" bonds may be single or double bonds;
with a triphenylphosphonium ylide of Formula 11:

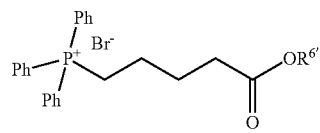

11 wherein
$R^{6'}$ may be as defined herein for $R^6$.

In some embodiments of Formula 8, the S/D bond between the carbon at position 8b1 and 8b2 is a single bond. In some embodiments of Formula 8, the S/D bond between the carbon at position 8b1 and 8b2 is a double bond. Some embodiments Formula 8 comprise a mixture of compounds in which a portion of the mixture of compounds comprise a single bond between the carbon at position 8b1 and the carbon at position 8b2 and another portion of the mixture of compounds comprise a double bond between the carbon at position 8b1 and the carbon at position 8b2. In some embodiments of Formula 8, the S/D bond between the carbon at position 8b3 and group X is a single bond. In some embodiments of Formula 8, the S/D bond between the carbon at position 8b3 and group X is a double bond. Some embodiments Formula 8 comprise a mixture of compounds in which a portion of the mixture of compounds comprise a single bond between the carbon at position 8b3 and group X and another portion of the mixture of compounds comprise a double bond between the carbon at position 8b3 and group X. Some embodiments of Formula 8 comprise a mixture of two or more compounds selected from the group consisting of:

a) compounds comprising i) a single bond between the carbon at position 8b1 and the carbon at position 8b2 and ii) a single bond between the carbon at position 8b3 and group X;

b) compounds comprising i) a single bond between the carbon at position 8b1 and the carbon at position 8b2 and ii) a double bond between the carbon at position 8b3 and group X;

c) compounds comprising i) a double bond between the carbon at position 8b1 and the carbon at position 8b2 and ii) a single bond between the carbon at position 8b3 and group X; and d) compounds comprising i) a double bond between the carbon at position 8b1 and the carbon at position 8b2 and ii) a double bond between the carbon at position 8b3 and group X.

Compounds of Formula 9 produced by reaction of compounds of Formula 8 with the triphenylphosphonium ylide of Formula 11 in the presence of the second base may be isolated or carried through to the next step without isolation.

The second base may be selected from the group consisting of metal hydrides and metal alkoxides. The second base may be selected from the group consisting of sodium hydride, sodium methoxide, potassium t-butoxide, sodium t-butoxide, and lithium t-butoxide The second base may be potassium t-butoxide. The reaction of the compounds of Formulas 8 and 11 may be conducted in the presence of a third solvent. The third solvent may be selected from the group consisting of C4-C12 cyclic and acyclic aliphatic and aromatic ethers. The third solvent may be selected from the group consisting of 1,2-dimethoxyethane, 1,2-diethoxyethane, diglyme, tetrahydrofuran, 1,4-dioxane, and anisole. The third solvent may be tetrahydrofuran.

Embodiments of Formula 9 in which $R^6$ is $R^7$ may be termed embodiments of Formula 9a. It is possible to prepare embodiments of Formula 9a as described above for Formula 9. Alternatively, a compound of Formula 9a may be prepared from a compound of Formula 9 wherein $R^6$ is H by reacting the compound of Formula 9 wherein $R^6$ is H with $R^7$-G, wherein R⁷ may be as defined above for one of Formulas 9a and/or 10 and G is a leaving group. G may be selected from the group consisting of: halogen atoms (e.g. chlorine, bromine and iodine) and/or sulfonyloxy groups (e.g. methanesulfonyloxy, trifluoromethanesulfonyloxy, p-toluenesulfonyloxy). In some embodiments, G may be selected from the group consisting of: chlorine, bromine, iodine, methanesulfonyloxy, trifluoromethanesulfonyloxy, p-toluenesulfonyloxy. In some embodiments, G may be bromine. The compound of Formula R⁷-G may be a benzyl halide whereby the benzyl is substituted or unsubstituted. The compound of Formula R⁷-G may be benzyl bromide. The reaction of R⁷-G with the compound of Formula 9 wherein R⁶ is H may be conducted in the presence of a third base. The third base may be organic or inorganic. The third base may be selected from the group consisting of triethylamine, diisopropylamine, diisopropylethylamine, pyridine and 1,8-diazabicyclo[5.4.0]undec-7-ene (DBU). The third base may be diisopropylamine. The third base may be pyridine.

According to illustrative embodiments of the present invention a compound of Formula 8, may be obtained by reduction, using a suitable reducing agent, of a compound of Formula 7:

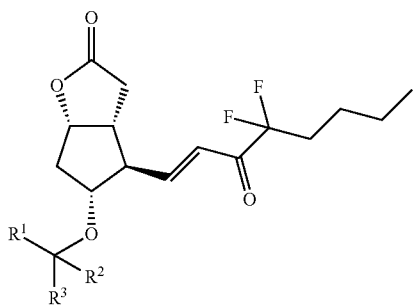

7 wherein $R^1$, $R^2$ and $R^3$ may be as defined above for any of Formulas 4, 5, 6, 8, 9, 9a, 10 and/or 10a.

The reducing agent may be selected from the group consisting of DIBAL-H, Red-Al, lithium tri-tert-butoxy aluminium hydride. The reducing agent may be DIBAL-H. The reduction of a compound of Formula 7 may occur in the presence of a second solvent. The second solvent may be toluene, xylene, dichloromethane or mixtures thereof. Often the second solvent is toluene. The reaction may be conducted at a temperature of about −100° C. to about 0° C. The reduction may produce a compound or composition comprising compounds of Formula 8 wherein the S/D bond between the carbon atom at position 8b1 and the carbon atom at position 8b2 of Formula 8 is a single bond, a double bond or mixtures thereof. The reduction may produce a compound of Formula 8 wherein X is OH, O or mixtures thereof and hence the S/D bond between the carbon atom at position 8b3 and group X may be a single bond (when X is OH), a double bond (when X is O) or mixtures thereof. All of these compounds may be used in the preparation of Lubiprostone.

According to illustrative embodiments of the present invention the compound of Formula 7 may be obtained by reacting, in the presence of a first base, a compound of Formula 6:

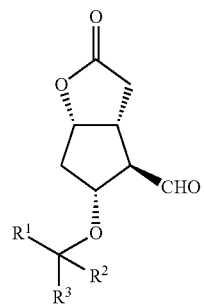

6 wherein $R^1$, $R^2$ and $R^3$ may be as defined above; with a 2-oxoalkyl phosphonate of the Formula 12:

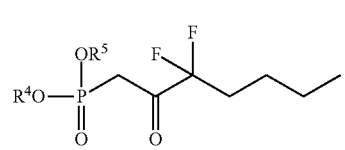

12 wherein $R^4$ and $R^5$ are independently a short chain alkyl.

In some embodiments of Formula 12, $R^4$ and $R^5$ are independently selected from the group consisting of: methyl, ethyl, propyl, isopropyl. In some embodiments of Formula 12, $R^4$ and $R^5$ are independently selected from the group consisting of: methyl and ethyl. In some embodiments of Formula 12, $R^4$ and $R^5$ are independently methyl.

The first base may be selected from alkali hydroxides (such as LiOH), $Zn(OH)_2$, mixtures of ammonia and alkali hydroxides, and mixtures thereof. If the first base is a mixture of at least two bases, one of the bases may be ammonia. If ammonia is used, the source of ammonia may be ammonium chloride. The first base may be $Zn(OH)_2$ or a mixture of bases comprising $Zn(OH)_2$.

The reaction between compounds of Formula 6 and Formula 12 may occur in the presence of a first solvent. The first solvent may be selected from the group consisting of: acyclic and cyclic aliphatic ethers and lower alkyl halides. The first solvent may comprise a mixture of methyl t-butyl ether and dichloromethane. The first solvent may further comprise water. The amount of water in the reaction may comprise from about 0.1% w/w to about 10% w/w.

According to illustrative embodiments of the present invention, Lubiprostone may be synthesized according to Scheme 2 starting from a compound of Formula 4.

SCHEME 2
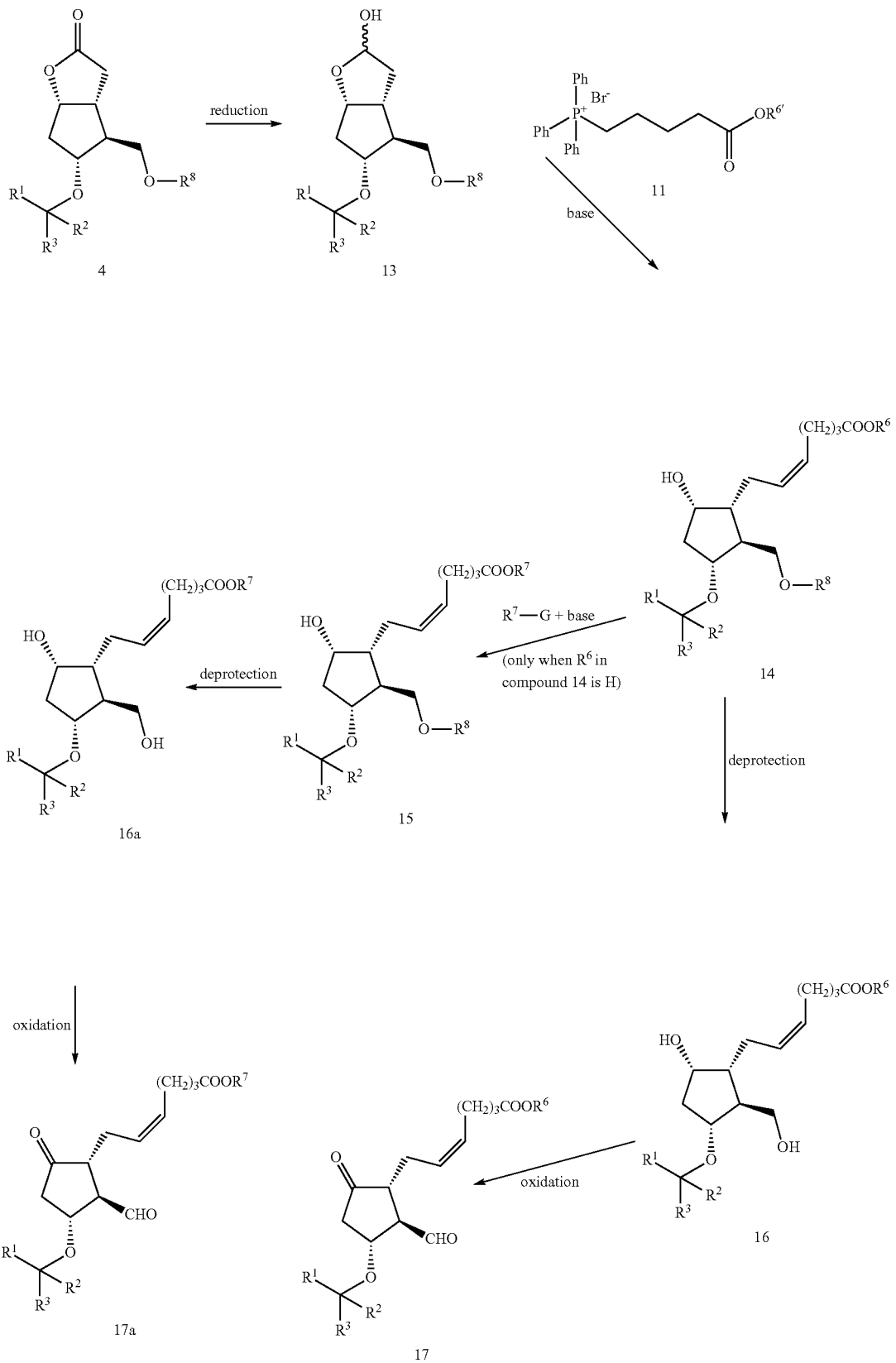

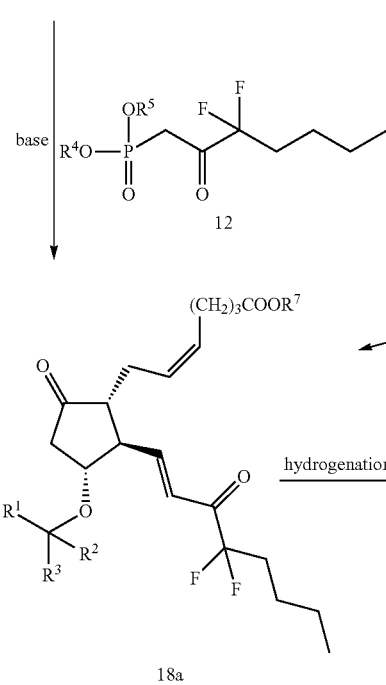

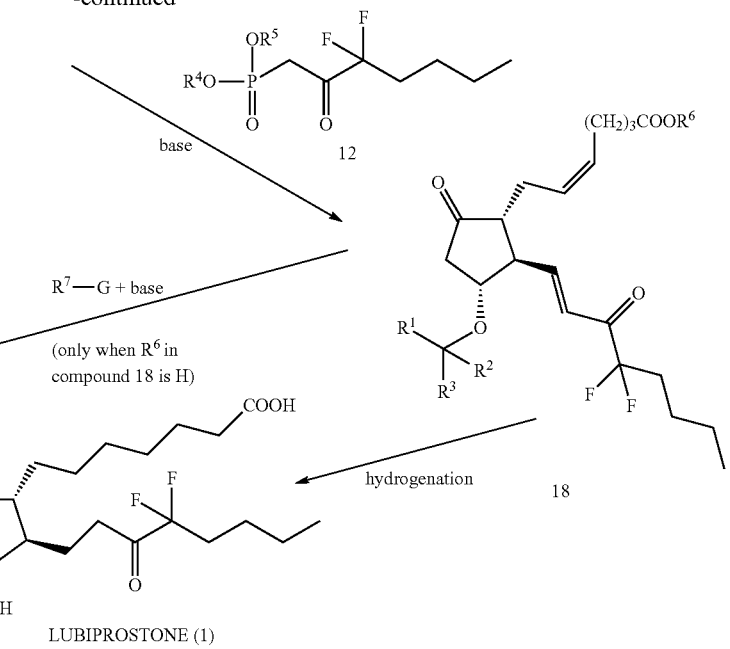

LUBIPROSTONE (1)

In Scheme 2 above, $R^1$, $R^2$ and $R^3$ are independently selected from the group consisting of H, alkyl, substituted alkyl, aryl, substituted aryl, arylalkyl, and substituted arylalkyl; wherein at least one of $R^1$, $R^2$ and $R^3$ is aryl or substituted aryl;

$R^4$ and $R^5$ are independently a short chain alkyl;

$R^6$ and $R^{6'}$ are independently H or $R^7$;

$R^7$ is $C(R^{1'})(R^{2'})(R^{3'})$, where $R^{1'}$, $R^{2'}$ and $R^{3'}$ may be as defined for $R^1$, $R^2$ and $R^3$, respectively;

$R^8$ is a silyl protecting group; and

G is a leaving group.

The compound of Formula 4 may be synthesized from a commercially available lactone of Formula 2 as above in Scheme 4.

In illustrative embodiments of the present invention the compound of Formula 13 may be obtained by reducing the compound of Formula 4.

The reducing agent for the reduction of the compound of Formula 4 to the compound of Formula 13 may be selected from the group consisting of DIBAL-H, Red-Al and lithium-tert-butoxy aluminum hydride. The reducing agent may be DIBAL-H. The reaction may be conducted using about 1 to about 2 equivalents of the reducing reagent. The reduction of the compound of Formula 4 may occur in a solvent selected from toluene, xylene, dichloromethane or mixtures thereof. Often the solvent is toluene or dichloromethane. The volume of solvent used may be about 10 volumes. The reaction may be conducted at a temperature of about −100° C. to about 0° C. Often the reaction is conducted at a temperature of about −78° C. to about −50° C.

In illustrative embodiments of the present invention the compound of Formula 14 may be obtained by reacting, in the presence of a base, the compound of Formula 13 with a 2-oxoalkyl phosphonate of Formula 11.

The base for use in the reaction between the compounds of Formulas 11 and 13 may be selected from the group consisting of metal hydrides and metal alkoxides. The base may be selected from the group consisting of sodium hydride, sodium methoxide, potassium t-butoxide, sodium t-butoxide and lithium t-butoxide. The base may be potassium t-butoxide. The reaction may be conducted using about 5 to about 6 equivalents of the base.

The reaction may be conducted using about 2.5 to about 3 equivalents of the selected triphenylphosphonium ylide.

The reaction of the compounds of Formulas 11 and 13 may be conducted in the presence of a solvent. The solvent may be selected from the group consisting of C4 to C12 cyclic and acyclic aliphatic and aromatic ethers. The solvent may be selected from the group consisting of 1,2-dimethoxyethane, 1,2-diethoxyethane, diglyme, tetrahydrofuran (THF), 1,4-dioxane and anisole. Often the solvent is tetrahydrofuran. The reaction may be conducted in about 10 to about 15 volumes of the solvent.

The reaction of the compounds of Formulas 11 and 13 may be conducted at a temperature of about 0° C. to about 30° C. Often the reaction is conducted at a temperature of about 20° C. to about 25° C.

A subset of the compounds of Formula 14 is compounds of Formula 15. It is possible to prepare embodiments of Formula 15 as describe above for Formula 14. Alternatively, a compound of Formula 15 may be prepared from a compound of Formula 14 wherein $R^6$ is H with $R^7$-G, wherein $R^7$ may be defined as above and G is a leaving group. G may be selected from the group consisting of: halogen atoms (e.g. chlorine, bromine and iodine) and/or sulfonyloxy groups (e.g. methanesulfonyloxy, trifluoromethanesulfonyloxy, p-toluenesulfonyloxy). In some embodiments, G may be selected from the group consisting of: chlorine, bromine, iodine, methanesulfonyloxy, trifluoromethanesulfonyloxy or p-toluenesulfonyloxy. In some embodiments, G may be bromine. The compound of Formula $R^7$-G may be a benzyl halide whereby the benzyl is substituted or unsubstituted. The compound of Formula $R^7$-G may be benzyl bromide. The reaction of $R^7$-G with the compound of Formula 14 wherein $R^6$ is hydrogen may be conducted in the presence of a base. The base may be an organic or inorganic base. The base may be selected from the group consisting of triethylamine, diisopropylamine, diisopropylethylamine, pyridine and DBU. The base may be diisopropylamine. The reaction may be conducted at a temperature of about 5° C. to about 30° C. Often the reaction is performed at about 15° C. to about 25° C.

In illustrative embodiments of the present invention the compound of Formula 16 may be obtained by deprotection of the compound of Formulas 14 or 15, wherein $R^8$ is TIPS, using TBAF.

In illustrative embodiments of the present invention the compound of Formula 17 is prepared by oxidation of a compound of Formula 16. Similarly, the compound of Formula 16a may be oxidized to a compound of Formula 17a.

The oxidation of a compound of Formula 16 or 16a may occur in the presence of an oxidizing agent. The oxidizing agent may be selected from the group consisting of Dess-Martin periodinane, $CrO_3$, $MnO_2$, TEMPO/sodium hypochlorite, $SO_3$/pyridine and oxalyl chloride/DMSO/triethylamine. The oxidizing agent may be Dess-Martin periodinane. The oxidizing agent may be oxalyl chloride/DMSO/triethylamine. Depending on the reagent used, the reaction may be performed using about 2 to about 3 equivalents of the oxidizing agent. The oxidation may occur in the presence of a solvent such as dichloromethane, DSMO or mixtures thereof. Often, the solvent is dichloromethane. The reaction may be conducted in about 10 volumes of solvent. The reaction may be conducted at a temperature of about −70° C. to about −78° C.

In illustrative embodiments of the present invention the compound of Formula 18 is prepared by reacting, in the presence of a base, the compound of Formula 17, with a 2-oxoalkyl phosphonate of the Formula 12:

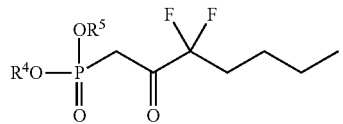

12 wherein $R^4$ and $R^5$ are independently a short chain alkyl. Similarly, the compound of Formula 18a may be prepared from the compound of Formula 17a.

In some embodiments of the compound of Formula 12, $R^4$ and $R^5$ are independently selected from the group consisting of: methyl, ethyl, propyl or isopropyl. In some embodiments of the compound of Formula 12, $R^4$ and $R^5$ are independently selected from the group consisting of methyl and ethyl. In some embodiments of the compound of Formula 12, $R^4$ and $R^5$ are independently methyl.

The base used in the reaction between the compound of Formula 17 and the compound of Formula 12 or used in the reaction between the compound of Formula 17a and the compound of Formula 12 may be selected from alkali hydroxides (such as lithium hydroxide), $Zn(OH)_2$, mixtures of ammonia and alkali hydroxides, and mixtures thereof. If the base is a mixture of at least two bases, one of the bases may be ammonia. If ammonia is used, the source of ammonia may be ammonia chloride. The base may be $Zn(OH)_2$. The reaction may be conducted using about 1 to about 2 equivalents of the base.

The reaction between the compounds of Formulas 17 and 12 or the compounds of Formulas 17a and 12 may be conducted using about 1 to about 3 equivalents of the selected triphenylphosphonium ylide. Often the reaction is performed using about 1 to about 1.2 equivalents of the ylide.

The reaction between the compounds of Formulas 17 and 12 or the compounds of Formulas 17a and 12 may occur in the presence of a solvent. The solvent may be selected from the group consisting of: acyclic and cyclic aliphatic ethers and lower alkyl halides. The solvent may comprise a mixture of methyl t-butyl ether and dichloromethane. The solvent may further comprise water. The amount of water in the reaction may comprise from about 0.1% w/w to about 10% w/w. The reaction may be conducted in about 10 volumes to about 15 volumes of the solvent. The reaction may be conducted at a temperature of about 0° C. to about 30° C. Often the reaction is conducted at a temperature of about 20° C. to about 25° C.

According to illustrative embodiments of the present invention, Lubiprostone may be synthesized according to Scheme 3 starting from the compound of Formula 15 or the compound of Formula 14a wherein $R^6$ is $R^7$.

Scheme 3

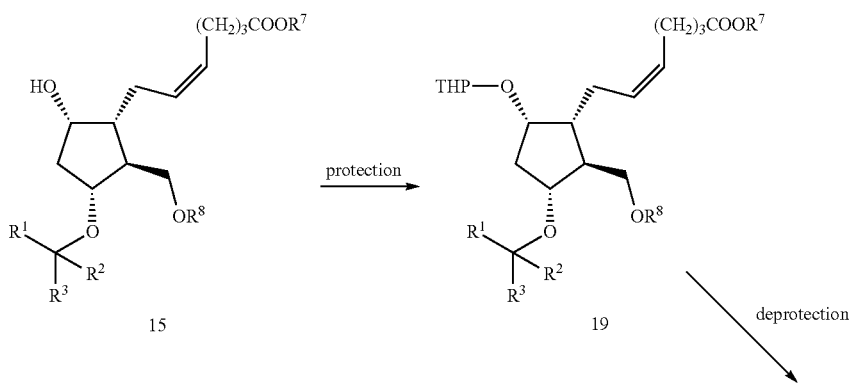

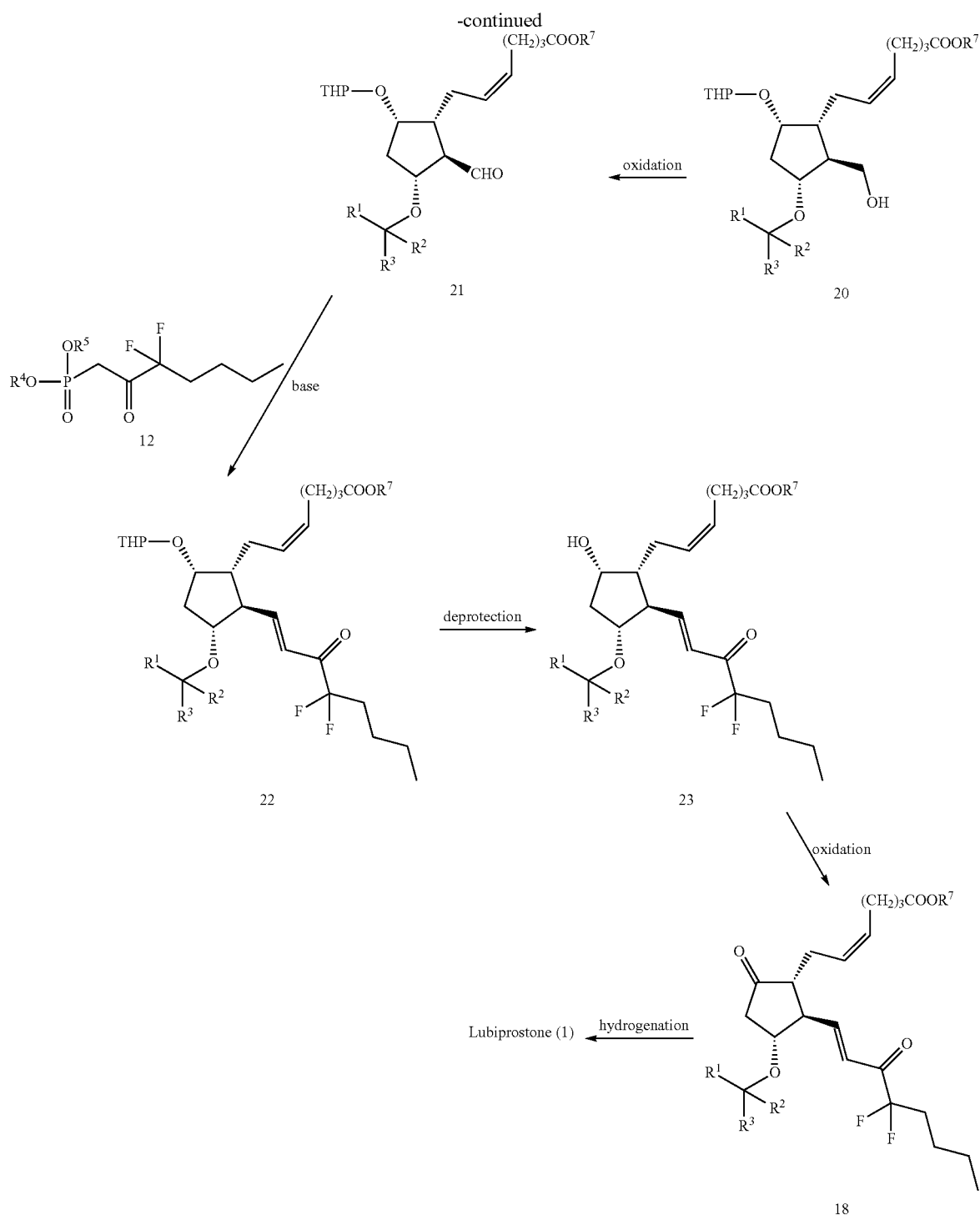

In Scheme 3 above, $R^1$, $R^2$ and $R^3$ are independently selected from the group consisting of H, alkyl, substituted alkyl, aryl, substituted aryl, arylalkyl, and substituted arylalkyl; wherein at least one of $R^1$, $R^2$ and $R^3$ is aryl or substituted aryl;

$R^4$ and $R^5$ are independently a short chain alkyl;

$R^7$ is $C(R^{1'})(R^{2'})(R^{3'})$, where $R^{1'}$, $R^{2'}$ and $R^{3'}$ may be as defined for $R^1$, $R^2$ and $R^3$, respectively;

$R^8$ is a silyl protecting group; and

THP is tetrahydropyranyl.

The compound of Formula 15 may be synthesized as described above in Scheme 2.

In illustrative embodiments of the present invention the compound of Formula 19 may be obtained by protection, using a suitable protecting agent, of the compound of Formula 15. The protecting agent may be dihydropyran.

In illustrative embodiments of the present invention the compound of Formula 20 may be obtained by deprotection of the compound of Formula 19 using TBAF.

In illustrative embodiments of the present invention the compound of Formula 21 is prepared by oxidation of the compound of Formula 20.

The oxidation of the compound of Formula 20 may occur in the presence of an oxidizing agent. The oxidizing agent may be selected from the group consisting of Dess-Martin periodinane, $CrO_3$, $MnO_2$, TEMPO/sodium hypochlorite, $SO_3$/pyridine and oxalyl chloride/DMSO/triethylamine. The oxidizing agent may be Dess-Martin periodinane. The oxidizing agent may be $SO_3$/pyridine. The oxidation may occur in the presence of a solvent such as dichloromethane, DSMO or mixtures thereof. Often, the solvent is dichloromethane.

In illustrative embodiments of the present invention the compound of Formula 22 is prepared by reacting, in the presence of a base, the compound of Formula 21 with a 2-oxoalkyl phosphonate of the Formula 12:

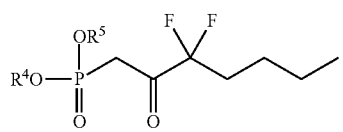

12 wherein $R^4$ and $R^5$ are independently a short chain alkyl.

In some embodiments of Formula 12, $R^4$ and $R^5$ are independently selected from the group consisting of: methyl, ethyl, propyl or isopropyl. In some embodiments of Formula 12, $R^4$ and $R^5$ are independently selected from the group consisting of methyl and ethyl. In some embodiments of Formula 12, $R^4$ and $R^5$ are independently methyl.

The base used in the reaction of the compound of Formula 21 with the compound of Formula 12 may be selected from alkali hydroxides (such as lithium hydroxide), $Zn(OH)_2$, mixtures of ammonia and alkali hydroxides, and mixtures thereof. If the base is a mixture of at least two bases, one of the bases may be ammonia. If ammonia is used, the source of ammonia may be ammonium chloride. The base may be $Zn(OH)_2$. The base may be lithium hydroxide.

The reaction between compounds of Formulas 17 and 12 may occur in the presence of a solvent. The solvent may be selected from the group consisting of: acyclic and cyclic aliphatic ethers and lower alkyl halides. The solvent may comprise a mixture of methyl t-butyl ether and dichloromethane. The solvent may further comprise water. The amount of water in the reaction may comprise from about 0.1% w/w to about 10% w/w.

In illustrative embodiments of the present invention the compound of Formula 23 may be obtained by deprotection of the compound of Formula 22 using pyridinium p-toluenesulfonate.

In illustrative embodiments of the present invention the compound of Formula 18 is prepared by oxidation of the compound of Formula 23.

The oxidation of the compound of Formula 23 may occur in the presence of an oxidizing agent. The oxidizing agent may be selected from the group consisting of Dess-Martin periodinane, $CrO_3$, $MnO_2$, TEMPO/sodium hypochlorite, $SO_3$/pyridine and oxalyl chloride/DMSO/triethylamine. The oxidizing agent may be Dess-Martin periodinane. The oxidation may occur in the presence of a solvent such as dichloromethane, DSMO or mixtures thereof. Often, the solvent is dichloromethane.

Within the reaction Schemes 1, 2, 3 and 4 there are many similar reactions types that a person of skill in the art will recognize as being similar. In such circumstances, it is to be understood that the reaction conditions described for one such reaction type may be applied to another such reaction type in a different reaction Scheme. Those reactions in which the compound of Formula 11, the compound of Formula 12 or the compound $R^7$-G is a reactant are examples of such similar reaction types.

Furthermore, a person of skill in the art will understand that not all 'protection' reactions, not all 'deprotection' reactions, not all 'oxidation' reactions and not all 'reduction' reactions are necessarily the same and careful consideration of the reactants and products must be made prior to applying conditions and reactants from one Scheme to another.

EXAMPLES

The following examples are illustrative of some of the embodiments of the invention described herein. These examples should not be considered to limit the spirit or scope of the invention in any way.

Example 1

Preparation of (3aR,4S,5R,6aS)-hexahydro-5-hydroxy-4-(triisopropylsilyloxymethyl)-2H-cyclopenta[b]furan-2-one (3, $R^8$ is TIPS): To a suspension of compound 2 (60.5 g, 0.352 mol) in dichloromethane (5 vol) was added imidazole (28.8 g, 0.422 mol) followed by TIPS-Cl (78.2 mL, 0.37 mol). The suspension was stirred for about 15 h. After the consumption of the starting material, the reaction mixture was cooled to 0° C., water (2 vol) was added and the pH adjusted to 3-4 using 1N HCl. The organic layer was separated, washed with water (to pH 5-6), and brine, dried over $Na_2SO_4$ and then concentrated to dryness to yield (3aR,4S,5R,6aS)-hexahydro-5-hydroxy-4-(triisopropylsilyloxymethyl)-2H-cyclopenta[b]furan-2-one (3, $R^8$ is TIPS) as a clear oil in quantitative yield.

$^1$H NMR (CDCl$_3$): δ 1.05 (m, 21H), 1.99 (m, 2H), 2.42-2.55 (m, 3H), 2.65 (m, 1H), 2.78 (m, 1H), 3.69 (m, 1H), 3.79 (m, 1H), 4.12 (m, 1H), 4.85 (m, 1H).

Example 2

Preparation of (3aR,4S,5R,6aS)-hexahydro-4-(triisopropylsilyloxymethyl)-5-(phenylmethoxy)-2H-cyclopenta[b]furan-2-one (4, $R^1$ is phenyl, $R^2$ and $R^3$ are H, and $R^8$ is TIPS): To suspension of 60% NaH (17 g, 0.424 mol) in anhydrous tetrahydrofuran (500 mL) at 0° C. was slowly added a solution of (3aR,4S,5R,6aS)-hexahydro-5-hydroxy-4-(triisopropylsilyloxymethyl)-2H-cyclopenta[b]furan-2-one (3, $R^8$ is TIPS, 116 g, 0.354 mol) in tetrahydrofuran (500 ml). The mixture was then stirred at 0° C. for 0.5 h and then allowed to warm to room temperature for 1 h. The reaction mixture was again cooled to 0° C., and benzylbromide (76 mL, 0.64 mol) and Bu$_4$NI (26 g, 0.08 mol) were added. After stirring for 15 h at room temperature, the reaction mixture was then cooled to 0° C. before quenching with saturated ammonium chloride solution (2 vol). The organic layer was separated, washed with brine, dried over $Na_2SO_4$ and then concentrated to dryness under vacuum to yield crude compound 4, which was further purified by column chromatography [35% ethyl acetate in heptanes] to produce pure compound (3aR,4S,5R,6aS)-hexahydro-4-(triisopropylsilyloxymethyl)-5-(phenylmethoxy)-2H-cyclopenta[b]furan-2-one (4, $R^1$ is phenyl, $R^2$ and $R^3$ are H, and $R^8$ is TIPS) in 80% yield.

$^1$H NMR (CDCl$_3$): δ 1.05 (m, 21H), 2.18 (m, 3H), 2.58 (m, 1H), 2.79 (m, 2H), 3.65 (m, 2H), 3.96 (m, 1H), 4.54 (dd, J=48.1, 11.7 Hz, 2H), 4.95 (m, 1H), 7.26 (m, 5H).

Example 3

Preparation of (3aR,4S,5R,6aS)-hexahydro-4-(hydroxymethyl)-5-(phenylmethoxy)-2H-cyclopenta[b]furan-2-one (5, $R^1$ is phenyl, and $R^2$ and $R^3$ are H): To a solution of (3aR,4S, 5R,6aS)-hexahydro-4-(triisopropylsilyloxymethyl)-5-(phenylmethoxy)-2H-cyclopenta[b]furan-2-one (4, $R^1$ is phenyl, $R^2$ and $R^3$ are H, and $R^8$ is TIPS, 49 g, 0.117 mol) in tetrahydrofuran (7 vol) at 0° C. was added TBAF (128 mL, 0.129 mol) and the mixture was stirred for 2 h. After completion of the reaction, the reaction mixture was concentrated to dryness and purified by column chromatography [55% ethyl acetate in heptanes] to yield (3aR,4S,5R,6aS)-hexahydro-4-(hydroxymethyl)-5-(phenylmethoxy)-2H-cyclopenta[b]furan-2-one (5, $R^1$ is phenyl, and $R^2$ and $R^3$ are H) in quantitative yield. $^1$H NMR (CDCl$_3$): δ 2.12 (m, 3H), 2.53 (m, 2H), 2.74 (m, 2H), 3.51 (m, 2H), 3.89 (m, 1H), 4.48 (dd, J=47.9, 11.5 Hz, 2H), 4.92 (m, 1H), 7.27 (m, 5H).

Example 4

Preparation of (3aR,4R,5R,6aS)-hexahydro-2-oxo-5-(phenyl methoxy)-2H-cyclopenta[b]furan-4-carboxaldehyde (6, $R^1$ is phenyl, and $R^2$ and $R^3$ are H): To a solution of oxalyl chloride (3.3 mL, 38.1 mmoL) in dichloromethane (35 mL) at −78° C., was added DMSO (5.4 mL, 76.3 mmoL) and the mixture was stirred for 15 min. A solution of (3aR,4S,5R,6aS)-hexahydro-4-(hydroxymethyl)-5-(phenylmethoxy)-2H-cycloenta[b]furan-2-one (5, $R^1$ is phenyl, and $R^2$ and $R^3$ are H, 5 g, 19 mmoL) in dichloromethane (35 mL) was then slowly added at −78° C. and the reaction mixture stirred for 0.5 h. Triethylamine (24 mL, 170 mmoL) was added at −78° C. and the reaction mixture stirred for 0.5 h. After completion of the reaction, the reaction mixture was washed with water (20 mL), and the organic layer was concentrated to dryness under vacuum to yield (3aR,4R,5R,6aS)-hexahydro-2-oxo-5-(phenylmethoxy)-2H-cyclopenta[b]furan-4-carboxaldehyde (6, $R^1$ is phenyl, and $R^2$ and $R^3$ are H) in 80% yield.

$^1$H NMR (CDCl$_3$): δ 1.81 (m, 1H), 2.49 (m, 2H), 2.89 (m, 1H), 3.11 (m, 1H), 3.37 (m, 1H), 4.33 (m, 1H), 4.35-4.65 (dd, J=47.8, 11.7 Hz, 2H), 5.04 (t, J=6.3 Hz, 1H), 7.28 (m, 5H), 9.65 (s, 1H).

Example 5

Preparation of (3aR,4R,5R,6aS)-4-((E)-4,4-difluoro-3-oxo-1-octenyl)-2-oxo-5-(phenylmethoxy)hexahydro-2H-cyclopenta[b]furan (7, $R^1$ is phenyl, and $R^2$ and $R^3$ are H): To a solution of dimethyl(3,3-difluoro-2-oxoheptyl)phosphonate (6.9 g, 26.5 mmoL) in MTBE (30 mL) was added LiOH.H$_2$O (1.11 g, 26.5 mmoL) and the mixture was stirred under nitrogen for 1 h. A solution of (3aR,4R,5R,6aS)-hexahydro-2-oxo-5-(phenylmethoxy)-2H-cyclopenta[b]furan-4-carboxaldehyde (6, $R^1$ is phenyl, and $R^2$ and $R^3$ are H, 6 g, 23.1 mmoL) in dichloromethane (30 mL) was added followed by NH$_4$Cl (370 mg, 6.93 mmoL), 0.2 mL water and then the mixture was stirred for 12 h. After completion of the reaction, the reaction was then quenched with a saturated NH$_4$Cl solution (12 mL). The organic layer was separated, washed with brine, dried over Na$_2$SO$_4$ and concentrated to dryness under vacuum. The crude material was further purified by column chromatography [25% ethyl acetate in heptanes] to yield (3aR,4R,5R,6aS)-4-((E)-4,4-difluoro-3-oxo-1-octenyl)-2-oxo-5-(phenylmethoxy)hexahydro-2H-cyclopenta[b]furan (7, $R^1$ is phenyl, and $R^2$ and $R^3$ are H) in 56% yield.

$^1$H NMR (CDCl$_3$): δ 0.92 (t, J=6.9 Hz, 3H), 1.31-1.49 (m, 4H), 1.91-2.08 (m, 2H), 2.19-2.73 (m, 3H), 2.77-2.94 (m, 3H), 3.88-3.94 (m, 1H), 4.51 (dd, J=43.8, 11.8 Hz, 2H), 4.79-5.01 (m, 1H), 6.59 (d, J=15.7 Hz, 1H), 6.96 (dd, J=15.7, 7.8 Hz, 1H), 7.26-7.56 (m, 5H).

Example 6

Preparation of (3aR,4R,5R,6aS)-4-((E)-4,4-difluoro-3-oxo-1-octenyl)-2-oxo-5-(phenylmethoxy) hexahydro-2H-cyclopenta[b]furan (7, $R^1$ is phenyl, and $R^2$ and $R^3$ are H): To a mixture of dimethyl(3,3-difluoro-2-oxoheptyl)phosphonate (210 mg, 0.81 mmoL) in MTBE/H$_2$O (3/0.1 mL) was added Zn(OH)$_2$ (100 mg, 0.81 mmoL) and the mixture was stirred under nitrogen for 1 h. A solution of (3aR,4R,5R,6aS)-hexahydro-2-oxo-5-(phenylmethoxy)-2H-cyclopenta[b]furan-4-carboxaldehyde (200 mg, 0.77 mmoL) in dichloromethane (3 mL) was added and the mixture was stirred for 24 h. After completion of the reaction, the reaction was then quenched with cold 1N HCl (12 mL). The organic layer was separated, washed with brine, dried over Na$_2$SO$_4$ and concentrated to dryness under vacuum. The crude material was further purified by column chromatography [25% ethyl acetate in heptanes] to yield (3aR,4R,5R,6aS)-4-((E)-4,4-difluoro-3-oxo-1-octenyl)-2-oxo-5-(phenylmethoxy)hexahydro-2H-cyclopenta[b]furan (7, $R^1$ is phenyl, and $R^2$ and $R^3$ are H) in 76% yield.

Example 7

Preparation of (3aR,4R,5R,6aS)-4-((E)-4,4-difluoro-3-hydroxy-1-octenyl)-5-(phenylmethoxy)hexahydro-2H-cyclopenta[b]furan-2-ol (8, $R^1$ is phenyl, and $R^2$ and $R^3$ are H, the S/D bond between the carbon at position 8b1 and the carbon at position 8b2 is a double bond, the S/D bond between the carbon at position 8b3 and group X is a single bond and X is OH): To a solution of (3aR,4R,5R,6aS)-4-((E)-4,4-difluoro-3-oxo-1-octenyl)-2-oxo-5-(phenylmethoxy) hexahydro-2H-cyclopenta[b]furan (7, $R^1$ is phenyl, and $R^2$ and $R^3$ are H, 2.5 g, 6.4 mmoL) in toluene (25 mL) at −78° C. was slowly added a solution of 1M DIBAL-H in dichloromethane (16 mmoL) over 10 min. The reaction mixture was stirred for 2 h. After completion of the reaction, methanol (3 mL) was added, followed by saturated sodium potassium tartrate solution (30 mL) and the mixture was stirred for 1 h while allowed to warm to room temperature. The organic layer was separated and the aqueous layer was extracted with ethyl acetate (30 mL). The combined organic phase was washed with brine, dried over Na$_2$SO$_4$ and then concentrated to dryness under vacuum. The crude material was further purified by column chromatography to yield (3aR,4R,5R, 6aS)-4-((E)-4,4-difluoro-3-hydroxy-1-octenyl)-5-(phenylmethoxy)hexahydro-2H-cyclopenta[b]furan-2-ol (8, $R^1$ is phenyl, and $R^2$ and $R^3$ are H, the S/D bond between the carbon at position 8b1 and the carbon at position 8b2 is a double bond, the S/D bond between the carbon at position 8b3 and group X is a single bond and X is OH) in 80% yield.

HRMS: Formula: $C_{22}H_{29}F_2O_3$: cal m/z: 379.2079 amu. found: 379.2091 amu.

Example 8

Preparation of (Z)-7-[(1R,2R,3R,5S)-2-((E)-4,4-difluoro-3-hydroxy-1-octenyl)-3-(phenylmethoxy)-5-hydroxycyclopentyl]-5-heptenoic acid (9, $R^1$ is phenyl, and $R^2$ and $R^3$ are H, $R^6$ is H, the S/D bond between the carbon at position 9b1 and the carbon at position 9b2 is a double bond, the S/D bond between the carbon at position 9b3 and group X is a single bond and X is OH): To a suspension of (4-carboxybutyl)

triphenyl phosphonium bromide (5 g, 11.37 mmoL) in anhydrous tetrahydrofuran (3 vol) was added potassium t-butoxide (2.56 g, 22.74 mmoL) at 0° C. and the mixture was stirred for 30 min before warming to room temperature for 30 min. A solution of (3aR,4R,5R,6aS)-4-((E)-4,4-difluoro-3-hydroxy-1-octenyl)-5-(phenylmethoxy)hexahydro-2H-cyclopenta[b]furan-2-ol (8, $R^1$ is phenyl, and $R^2$ and $R^3$ are H, the S/D bond between the carbon at position 8b1 and the carbon at position 8b2 is a double bond, the S/D bond between the carbon at position 8b3 and group X is a single bond and X is OH, 1.5 g, 3.8 mmoL) in tetrahydrofuran (5 mL) was added to the above mixture and the stirring continued for 3 h. After the completion of the reaction, 1 N HCl (15 mL) was added. The organic layer was separated and the aqueous layer was extracted with ethyl acetate (50 mL). The combined organic phase was washed with water and brine, dried over $Na_2SO_4$ and concentrated to dryness. Purified (Z)-7-[(1R,2R,3R,5S)-2-((E)-4,4-difluoro-3-hydroxy-1-octenyl)-3-(phenylmethoxy)-5-hydroxycyclopentyl]-5-heptenoic acid (9, $R^1$ is phenyl, and $R^2$ and $R^3$ are H, $R^6$ is H, the S/D bond between the carbon at position 9b1 and the carbon at position 9b2 is a double bond, the S/D bond between the carbon at position 9b3 and group X is a single bond and X is OH) was obtained by chromatographic purification in 90% yield.

HRMS: Formula: $C_{27}H_{39}F_2O_5$: cal m/z: 481.2760 amu. found: 481.2756 amu.

Example 9

Preparation of benzyl (Z)-7-[(1R,2R,3R,5S)-2-((E)-4,4-difluoro-3-hydroxy-1-octenyl)-3-(phenylmethoxy)-5-hydroxycyclopentyl]-5-heptenoate (9, $R^1$ is phenyl, and $R^2$ and $R^3$ are H, $R^6$ is $R^7$ in which $R^1$ is phenyl, and $R^2$ and $R^3$ are H, the S/D bond between the carbon at position 9b1 and the carbon at position 9b2 is a double bond, the S/D bond between the carbon at position 9b3 and group X is a single bond and X is OH): To a solution of compound (Z)-7-[(1R,2R,3R,5S)-2-((E)-4,4-difluoro-3-hydroxy-1-octenyl)-3-(phenylmethoxy)-5-hydroxycyclopentyl]-5-heptenoic acid (9, $R^1$ is phenyl, and $R^2$ and $R^3$ are H, $R^6$ is H, the S/D bond between the carbon at position 9b1 and the carbon at position 9b2 is a double bond, the S/D bond between the carbon at position 9b3 and group X is a single bond and X is OH, 170 mg, 0.36 mmoL) was added diisopropylamine (0.1 mL, 0.53 mmoL) and benzyl bromide (0.065 mL, 0.53 mmoL) under nitrogen. After the completion of the reaction, the reaction mixture was concentrated to dryness and purified by column chromatography to yield benzyl (Z)-7-[(1R,2R,3R,5S)-2-((E)-4,4-difluoro-3-hydroxy-1-octenyl)-3-(phenylmethoxy)-5-hydroxycyclopentyl]-5-heptenoate (9, $R^1$ is phenyl, and $R^2$ and $R^3$ are H, $R^6$ is $R^7$ in which $R^{1'}$ is phenyl, and $R^{2'}$ and $R^{3'}$ are H, the S/D bond between the carbon at position 9b1 and the carbon at position 9b2 is a double bond, the S/D bond between the carbon at position 9b3 and group X is a single bond and X is OH) in 95% yield.

Example 10

Preparation of (Z)-7-[(1R,2R,3R)-2-((E)-4,4-difluoro-3-oxo-1-octenyl)-3-(phenylmethoxy)-5-oxocyclopentyl]-5-heptenoic acid (10, $R^1$ is phenyl, and $R^2$ and $R^3$ are H, $R^6$ is H, the S/D bond between the carbon at position 9b1 and the carbon at position 9b2 is a double bond): To a solution of (Z)-7-[(1R,2R,3R,5S)-2-((E)-4,4-difluoro-3-hydroxy-1-octenyl)-3-(phenylmethoxy)-5-hydroxycyclopentyl]-5-heptenoic acid (9, $R^1$ is phenyl, and $R^2$ and $R^3$ are H, $R^6$ is H, the S/D bond between the carbon at position 9b1 and the carbon at position 9b2 is a double bond, the S/D bond between the carbon at position 9b3 and group X is a single bond and X is OH, 90 mg, 0.16 mmoL) in dichloromethane (5 mL) was added Dess-martin reagent (150 mg, 0.35 mmoL) and the mixture was stirred for 2 h. After the completion of the reaction, a saturated $NaHCO_3$ solution (5 mL) was added and the layers separated. The organic layer was washed with brine, dried over $Na_2SO_4$ and then concentrated to dryness under vacuum. Purified (Z)-7-[(1R,2R,3R)-2-((E)-4,4-difluoro-3-oxo-1-octenyl)-3-(phenylmethoxy)-5-oxocyclopentyl]-5-heptenoic acid (10, $R^1$ is phenyl, and $R^2$ and $R^3$ are H, $R^6$ is H, the S/D bond between the carbon at position 9b1 and the carbon at position 9b2 is a double bond) was obtained by chromatographic purification in 75% yield.

$^1$H NMR (CDCl$_3$): δ 0.92 (t, J=7.1 Hz, 3H), 1.33-1.50 (m, 4H), 1.61-1.72 (m, 2H), 1.95-2.08 (m, 4H), 2.20-2.44 (m, 6H), 2.75-2.91 (m, 2H), 3.97-4.03 (m, 1H), 4.49-4.59 (m, 2H), 5.25-5.32 (m, 1H), 5.41-5.47 (m, 1H), 6.67 (d, J=16.1 Hz, 1H), 7.12 (dd, J=15.5, 8.5 Hz, 1H), 7.26-7.36 (m, 5H).

Example 11

Preparation of benzyl (Z)-7-[(1R,2R,3R)-2-((E)-4,4-difluoro-3-oxo-1-octenyl)-3-(phenylmethoxy)-5-oxocyclopentyl]-5-heptenoate (10, $R^1$ is phenyl, and $R^2$ and $R^3$ are H, $R^6$ is $R^7$ in which $R^1$ is phenyl, and $R^2$ and $R^3$ are H, the S/D bond between the carbon at position 9b1 and the carbon at position 9b2 is a double bond): To a solution of benzyl (Z)-7-[(1R,2R,3R,5S)-2-((E)-4,4-difluoro-3-hydroxy-1-octenyl)-3-(phenylmethoxy)-5-hydroxycyclopentyl]-5-heptenoic acid (9, $R^1$ is phenyl, and $R^2$ and $R^3$ are H, $R^6$ is $R^7$ in which $R^1$ is phenyl, and $R^2$ and $R^3$ are H, the S/D bond between carbon 6 and carbon 7 is a double bond, the S/D bond between the carbon at position 9b3 and group X is a single bond and X is OH, 90 mg, 0.16 mmoL) in dichloromethane (5 mL) was added Dess-Martin reagent (150 mg, 0.35 mmoL) and the mixture was stirred for 2 h. After the completion of the reaction, saturated $NaHCO_3$ solution (5 mL) was added, the layers were separated and the organic layer was washed with brine, dried over $Na_2SO_4$ and then concentrated to dryness. Purified benzyl (Z)-7-[(1R,2R,3R)-2-((E)-4,4-difluoro-3-oxo-1-octenyl)-3-(phenylmethoxy)-5-oxocyclopentyl]-5-heptenoate (10, $R^1$ is phenyl, and $R^2$ and $R^3$ are H, $R^6$ is $R^7$ in which $R^{1'}$ is phenyl, and $R^{2'}$ and $R^{3'}$ are H, the S/D bond between the carbon at position 9b1 and the carbon at position 9b2 is a double bond) was obtained by chromatographic purification in 75% yield.

$^1$H NMR (CDCl$_3$): δ 0.91 (t, J=7.2 Hz, 3H), 1.22-2.48 (m, 16H), 2.73-2.89 (m, 2H), 3.98 (dd, J=16.0, 8.4 Hz, 1H), 4.53 (dd, J=28.3, 11.8 Hz, 2H), 5.10 (s, 2H), 5.22-5.28 (m, 1H), 5.40-5.45 (m, 1H), 6.66 (d, J=15.5 Hz, 1H), 7.10 (dd, J=15.6, 8.5 Hz, 1H), 7.25-7.39 (m, 10H).

Example 12

Preparation of (2S*/R*,3aR,4S,5R,6aS)-5-benzyloxy-4-[(thisopropylsilyloxy)methyl]hexahydro-2H-cyclopenta[b]furan-2-ol (13, $R^1$ is phenyl, $R^2$ and $R^3$ are H and $R^8$ is TIPS): To a solution of (3aR,4S,5R,6aS)-5-benzyloxy-4-[(triisopropylsilyloxy)methyl]hexahydro-2H-cyclopenta[b]furan-2-one (4, $R^1$ is phenyl, $R^2$ and $R^3$ are H and $R^8$ is TIPS, 15.00 g, 35.82 mmoL) in dichloromethane (10 volumes) at −78° C. was added DIBAL-H (39.41 mmoL) dropwise. The mixture was stirred at −78° C. for 1 hour. Saturated aqueous sodium potassium L-tartrate (1 volume) was added and the mixture was allowed to warm to 0-5° C. Saturated aqueous sodium potassium L-tartrate (6 volumes) was added and the mixture was allowed to warm to room temperature. The mixture was stirred at room temperature for 1-2 hours and filtered through Celite®. The layers were separated; the aqueous layer was extracted with dichloromethane (4 volumes) and the combined organic layers were washed with brine (2×4 volumes). The organic layer was concentrated to dryness to yield a mixture of isomers of (2S*/R*,3aR,4S,5R,6aS)-5-benzyloxy-4-[(thisopropylsilyloxy)methyl]hexahydro-2H-cyclopenta[b]furan-2-ol (13, $R^1$ is phenyl, $R^2$ and $R^3$ are H and $R^8$ is TIPS, 14.0 g) as a an oil.

$^1$H NMR (CDCl$_3$): δ 1.12-1.02 (m, 42H), 1.85-1.91 (m, 1H), 1.97-2.13 (m, 4H), 2.22-2.47 (m, 4H), 2.49-2.54 (m, 2H), 2.62-2.70 (m, 1H), 2.71-2.72 (m, 1H), 3.48-3.52 (m, 1H), 3.64-3.73 (m, 3H), 3.88-3.93 (m, 1H), 4.04-4.06 (m, 1H), 4.42-4.65 (m, 4H), 4.65-4.72 (m, 2H), 5.20-5.23 (m, 1H), 5.39-5.43 (m, 1H), 5.63-5.65 (m, 1H), 7.23-7.35 (m, 10H).

Example 13

Preparation of (5Z)-7-[(1R,2S,3R,5S)-3-benzyloxy-5-hydroxy-2-[(triisopropylsilyloxy)methyl]cyclopentyl]hept-5-enoic acid (14, $R^1$ is phenyl, $R^2$, $R^3$ and $R^6$ are H, and $R^8$ is TIPS): Potassium tert-butoxide (26.67 g, 237.7 mmoL) was added to a solution of (4-carboxyl)butyltriphenylphosphonium bromide (118.8 mmoL) in tetrahydrofuran (10 volumes) at 0-5° C. The suspension was warmed to room temperature. A solution of (2S*/R*,3aR,4S,5R,6aS)-5-benzyloxy-4-[(triisopropylsilyloxy)methyl]hexahydro-2H-cyclopenta[b]furan-2-ol (13, $R^1$ is phenyl, $R^2$ and $R^3$ are H and $R^8$ is TIPS, 20 g, 47.54 mmoL) in tetrahydrofuran (2 volumes) was added and the mixture was stirred at room temperature for about 2-4 hours. The mixture was cooled to 0-5° C., quenched with deionized water (0.5 volumes) and filtered through Celite®. To the filtrate was added 5% hydrochloric acid (5 volumes) and ethyl acetate (10 volumes). The layers were separated and the organic layer was concentrated to dryness. The residue was purified by column chromatography (35% ethyl acetate in heptanes to 60% ethyl acetate in heptanes) to yield (5Z)-7-[(1R,2S,3R,5S)-3-benzyloxy-5-hydroxy-2-[(triisopropylsilyloxy)methyl]cyclopentyl]hept-5-enoic acid (14, $R^1$ is phenyl, $R^2$, $R^3$ and $R^6$ are H and $R^8$ is TIPS) as an oil (80%).

$^1$H NMR (CDCl$_3$): δ 0.99-1.12 (m, 21H), 1.60-1.80 (m, 4H), 2.20-2.26 (m, 5H), 2.31-2.42 (m, 3H), 3.52 (dd, J=9.9, 6.3 Hz, 1H), 3.80 (dd, J=9.8, 4.0 Hz, 1H), 4.05 (apparent d, J=5.4 Hz, 1H), 4.13 (apparent t, J=3.8 Hz, 1H), 4.52 (dd, J=16.3, 11.9 Hz, 2H), 5.34-5.41 (m, 1H), 5.46-5.52 (m, 1H), 7.24-7.35 (m, 5H).

Example 14

Preparation of (5Z)-benzyl 7-[(1R,2S,3R,5S)-3-[benzyloxy-5-hydroxy-2-[(triisopropylsilyloxy)methyl]cyclopentyl]hept-5-enoate (15, $R^1$ is phenyl, $R^2$ and $R^3$ are H, $R^7$ is benzyl and $R^8$ is TIPS): To a solution of (5Z)-7-[(1R,2S,3R,5S)-3-benzyloxy-5-hydroxy-2-[(triisopropylsilyloxy)methyl]cyclopentyl]hept-5-enoic acid (14, $R^1$ is phenyl, $R^2$, $R^3$ and $R^6$ are H and $R^8$ is TIPS, 7.0 g, 14.0 mmoL) and diisopropylamine (2.8 mmoL) in dichloromethane (10 volumes) was added benzyl bromide (15.0 mmoL) at room temperature. The mixture was stirred at room temperature overnight. To the mixture was added deionized water (5 volumes). The layers were separated and the organic layer was concentrated to dryness to yield (5Z)-benzyl 7-[(1R,2S,3R,5S)-3-[benzyloxy-5-hydroxy-2-[(triisopropylsilyloxy)methyl]cyclopentyl]hept-5-enoate (15, $R^1$ is phenyl, $R^2$ and $R^3$ are H, $R^7$ is benzyl and $R^8$ is TIPS) as an oil (90%).

$^1$H NMR (CDCl$_3$): δ 0.99-1.11 (m, 21H), 1.58-2.25 (m, 9H), 2.32-2.39 (m, 3H), 2.53 (d, J=10.0 Hz, 1H), 3.51 (dd, J=9.9, 6.3 Hz, 1H), 3.80 (dd, J=9.9, 4.0 Hz, 1H), 4.03-4.16 (m, 2H), 4.47-4.56 (m, 2H), 5.10 (s, 2H), 5.32-5.52 (m, 2H), 7.24-7.41 (m, 10H).

Example 15

Preparation of (5Z)-benzyl 7-[(1R,2S,3R,5S)-3-benzyloxy-5-hydroxy-2-(hydroxymethyl)cyclopentyl]hept-5-enoate (16, $R^1$ is phenyl, $R^2$ and $R^3$ are H and $R^7$ is benzyl): To a solution of (5Z)-benzyl 7-[(1R,2S,3R,5S)-3-[benzyloxy-5-hydroxy-2-[(triisopropylsilyloxy)methyl]cyclopentyl]hept-5-enoate (15, $R^1$ is phenyl, $R^2$ and $R^3$ are H, $R^7$ is benzyl and $R^8$ is TIPS, 14.6 g, 28.9 mmoL) in tetrahydrofuran (5 volumes) at 0-5° C. was added tetra-n-butylammonium fluoride (1.0 M in tetrahydrofuran, 4.33 mmoL). The mixture was slowly warmed to room temperature and stirred overnight at room temperature. To the mixture was added ethyl acetate (10 volumes) and deionized water (5 volumes). The layers were separated and the organic layer was concentrated to dryness. The residue was purified by column chromatography (50% ethyl acetate in heptanes) to yield (5Z)-benzyl 7-[(1R,2S,3R,5S)-3-benzyloxy-5-hydroxy-2-(hydroxymethyl)cyclopentyl]hept-5-enoate (16, $R^1$ is phenyl, $R^2$ and $R^3$ are H and $R^7$ is benzyl) as an oil (10.1 g).

$^1$H NMR (CDCl$_3$): δ 1.44-2.49 (m, 13H), 2.56 (d, J=9.3 Hz, 1H), 3.40 (s, 1H), 3.69-3.71 (m, 1H), 3.97 (s, 1H), 4.09-4.12 (m, 1H), 4.51 (s, 2H), 5.09 (s, 2H), 5.33-5.53 (m, 2H), 7.24-7.33 (m, 10H).

Example 16

Preparation of (5Z)-benzyl 7-[(1R,2R,3R)-3-benzyloxy-2-formyl-5-oxocyclopentyl]hept-5-enoate (17, $R^1$ is phenyl, $R^2$ and $R^3$ are H and $R^7$ is benzyl): To a solution of oxalyl chloride (68.4 mmoL) in dichloromethane (10 volumes) at −78° C. was added DMSO (114.0 mmoL). The solution was stirred at −78° C. for 30-60 minutes followed by drop-wise addition of (5Z)-benzyl 7-[(1R,2S,3R,5S)-3-benzyloxy-5-hydroxy-2-(hydroxymethyl)cyclopentyl]hept-5-enoate (16, $R^1$ is phenyl, $R^2$ and $R^3$ are H and $R^7$ is benzyl, 10 g, 22.8 mmoL) in dichloromethane (10 volumes). The reaction mixture was stirred at −78° C. for 30 minutes at which time triethylamine (105.9 mmoL) was charged. The mixture was stirred at −78 to −60° C. for 4-6 hours followed by quenching with saturated aqueous ammonium chloride (10 volumes). The mixture was warmed to 0° C. The layers were separated; the organic layer was washed with saturated aqueous sodium carbonate, dried over sodium sulfate, filtered through Celite® and concentrated to dryness. The residue was purified by column chromatography (50% ethyl acetate in heptanes) to yield (5Z)-benzyl 7-[(1R,2R,3R)-3-benzyloxy-2-formyl-5-oxocyclopentyl]hept-5-enoate (17, $R^1$ is phenyl, $R^2$ and $R^3$ are H and $R^7$ is benzyl) as an oil (9.8 g).

$^1$H NMR (CDCl$_3$): δ 1.58-2.62 (m, 10H), 2.66-2.75 (m, 1H), 3.03-3.10 (m, 1H) 4.33 (dd, J=14.0, 7.0 Hz, 1H), 4.53 (dd, J=19.3, 11.7 Hz, 2H), 5.10 (s, 2H), 5.22-5.28 (m, 1H), 5.42-5.51 (m, 1H), 7.29-7.38 (m, 10H), 9.84 (s, 1H).

Example 17

Preparation of (5Z)-benzyl 7-[(1R,2R,3R)-3-benzyloxy-2-[(E)-4,4-difluoro-3-oxooct-1-enyl]-5-oxocyclopentypept-5-enoate (18, $R^1$ is phenyl and $R^2$, $R^3$ are H and $R^7$ is benzyl): To a mixture of zinc chloride (25.0 mmoL) in water (15 mL) at about 10° C. was added 50% sodium hydroxide (49.0 mmoL)

followed by water (5 mL). The mixture was stirred vigorously with a mechanical stirred at room temperature. To the mixture was added dimethyl(3,3-difluoro-2-oxoheptyl)phosphonate (17.0 mmoL) in tetrahydrofuran (15 mL). The mixture was stirred at room temperature for about an hour. To the mixture was added (5Z)-benzyl 7-[(1R,2R,3R)-3-benzyloxy-2-formyl-5-oxocyclopentyl]hept-5-enoate (17, $R^1$ is phenyl, $R^2$ and $R^3$ are H and $R^7$ is benzyl, 15.0 mmoL) in tetrahydrofuran (15 mL). The mixture was stirred at room temperature overnight. To the mixture was added dichloromethane (60 mL) and water (50 mL). The pH was adjusted to approximately 4 with 5 wt % hydrochloric acid. The layers were separated; the organic layer was dried over sodium sulfate, filtered through Celite® and concentrated to dryness. The residue was purified by column chromatography (40% ethyl acetate in heptanes) to yield (5Z)-benzyl 7-[(1R,2R,3R)-3-benzyloxy-2-[(E)-4,4-difluoro-3-oxooct-1-enyl]-5-oxocyclopentyl]hept-5-enoate (18, $R^1$ is phenyl and $R^2$, $R^3$ are H and $R^7$ is benzyl) as an oil (4.1 g).

$^1$H NMR (CDCl$_3$): δ 0.91 (t, J=7.2 Hz, 3H), 1.22-2.48 (m, 16H), 2.73-2.89 (m, 2H), 3.98 (dd, J=16.0, 8.4 Hz, 1H), 4.53 (dd, J=28.3, 11.8 Hz, 2H), 5.10 (s, 2H), 5.22-5.28 (m, 1H), 5.40-5.45 (m, 1H), 6.66 (d, J=15.5 Hz, 1H), 7.10 (dd, J=15.6, 8.5 Hz, 1H), 7.25-7.39 (m, 10H).

Example 18

Preparation of (2S*/R*,3aR,4S,5R,6aS)-5-benzyloxy-4-[(triisopropylsilyloxy)methyl]hexahydro-2H-cyclopenta[b]furan-2-ol (13, $R^1$ is phenyl, $R^2$ and $R^3$ are H and $R^8$ is TIPS): To a solution of (3aR,4S,5R,6aS)-5-benzyloxy-4-[(triisopropylsilyloxy)methyl]hexahydro-2H-cyclopenta[b]furan-2-one (4, $R^1$ is phenyl, $R^2$ and $R^3$ are H and $R^8$ is TIPS, 10.00 g, 23.89 mmoL) in toluene (68 mL) at −78° C. was added DIBAL-H (35.83 mL) dropwise. The mixture was stirred at −78° C. for 2 hours, quenched with methanol (155.28 mmoL) and allowed to warm to 20-25° C. To the mixture was added saturated aqueous sodium potassium tartrate (90 mL) and toluene (50 mL). The mixture was stirred for 1 hour. The layers were separated; the aqueous layer was extracted with toluene and the organic layers washed with water. The organic layer was dried over sodium sulfate, filtered through Celite® and concentrated to dryness to obtain (2S*/R*,3aR,4S,5R,6aS)-5-benzyloxy-4-[(triisopropylsilyloxy)methyl]hexahydro-2H-cyclopenta[b]furan-2-ol (13, $R^1$ is phenyl, $R^2$ and $R^3$ are H and $R^8$ is TIPS) as a pale yellow oil (8.70 g, 87%).

$^1$H NMR (CDCl$_3$): δ 1.12-1.02 (m, 42H), 1.85-1.91 (m, 1H), 1.97-2.13 (m, 4H), 2.22-2.47 (m, 4H), 2.49-2.54 (m, 2H), 2.62-2.70 (m, 1H), 2.71-2.72 (m, 1H), 3.48-3.52 (m, 1H), 3.64-3.73 (m, 3H), 3.88-3.93 (m, 1H), 4.04-4.06 (m, 1H), 4.42-4.65 (m, 4H), 4.65-4.72 (m, 2H), 5.20-5.23 (m, 1H), 5.39-5.43 (m, 1H), 5.63-5.65 (m, 1H), 7.23-7.35 (m, 10H).

Example 19

Preparation of (5Z)-benzyl 7-[(1R,2S,3R,5S)-3-[benzyloxy-5-hydroxy-2-[(triisopropylsilyloxy)methyl]cyclopentypentyl]-5-enoate (15, $R^1$ is phenyl, $R^2$ and $R^3$ are H, $R^7$ is benzyl and $R^8$ is TIPS): Potassium tert-butoxide (11.60 g, 103.40 mmoL) was added to a solution of (4-carboxybutyl)triphenylphosphonium bromide (22.92 g, 51.70 mmoL) in tetrahydrofuran (87 mL) at 0-5° C. The suspension was stirred at 0° C. for 5-10 minutes and warmed to 20-25° C. A solution of (2S*/R*,3aR,4S,5R,6aS)-5-benzyloxy-4-[(triisopropylsilyloxy)methyl]hexahydro-2H-cyclopenta[b]furan-2-ol (13, $R^1$ is phenyl and $R^2$, $R^3$ and $R^6$ are H, 8.70 g, 20.68 mmoL) in tetrahydrofuran (52 mL) was added and the reaction mixture was stirred at 20-25° C. for 2-4 hours. The suspension was quenched with water (70 mL) at 0-5° C. The tetrahydrofuran was removed under reduced pressure distillation. To the solution was added hydrochloric acid (1 M, 52 mL) and ethyl acetate (70 mL). The layers were separated; the aqueous layer was extracted with ethyl acetate and the organic layers were washed with water. The organic layer was dried over sodium sulfate, filtered through Celite® and concentrated to dryness. Column chromatography (10% ethyl to 70% ethyl acetate in heptane) gave as a colourless oil (7.08 g, 68%). A solution of this crude compound (7.08 g, 14.03 mmoL), diisopropylamine (6.8 mL, 39.28 mmoL) and benzyl bromide (4.7 mL, 39.28 mmoL) in acetonitrile (70 mL) was stirred at 20-25° C. for about 15 hours. The mixture was concentrated to dryness under reduced pressure. To the mixture was added ethyl acetate (70 mL) and water (70 mL). The layers were separated; the aqueous layer was extracted with ethyl acetate, the organic layers were treated with hydrochloric acid (1M, 70 mL) then with saturated sodium bicarbonate (70 mL). The organic phase was dried over sodium sulfate, filtered through Celite® and concentrated to dryness. Column chromatography (100% heptanes to 20% ethyl acetate in heptanes) gave (5Z)-benzyl 7-[(1R,2S,3R,5S)-3-[benzyloxy-5-hydroxy-2-[(triisopropylsilyloxy)methyl]cyclopentyl]hept-5-enoate (15, $R^1$ is phenyl, $R^2$ and $R^3$ are H, $R^7$ is benzyl and $R^8$ is TIPS) as a pale yellow oil (7.34 g, 82%).

$^1$H NMR (CDCl$_3$): δ 1.11-1.00 (m, 21H), 1.80-1.59 (m, 4H), 2.25-1.99 (m, 5H), 2.39-2.32 (m, 3H), 2.53 (d, 1H, J=9.8 Hz), 3.51 (dd, 1H, J=6.4, 9.8 Hz), 3.80 (dd, 1H, J=3.9, 9.8 Hz), 4.13-4.03 (m, 2H), 4.56-4.47 (m, 2H), 5.10 (s, 2H), 5.52-5.33 (m, 2H), 7.39-7.28 (m, 10H).

Example 20

Preparation of benzyl (Z)-7-[(1R,2S,3R,5S)-2-(triisopropylsilyloxymethyl)-3-(2-phenylmethoxy)-5-(2-tetrahydropyranyloxy)cyclopentyl]-5-heptanoate (19, $R^1$ is phenyl, $R^2$ and $R^3$ are H, $R^7$ is benzyl and $R^8$ is TIPS): To a solution of (5Z)-benzyl 7-[(1R,2S,3R,5S)-3-[benzyloxy-5-hydroxy-2-[(triisopropylsilyloxy)methyl]cyclopentyl]hept-5-enoate (15, $R^1$ is phenyl, $R^2$ and $R^3$ are H, $R^7$ is benzyl and $R^8$ is TIPS, 6.64 g, 11.16 mmoL) in dichloromethane (66 mL) at 0-5° C. were added dihydropyran (1.22 mL, 13.39 mmoL) and pyridinium p-toluenesulfonate (0.66 g, 2.63 mmoL). The mixture was stirred at 0-5° C. for 10-15 minutes and then at 20-25° C. for 7.5 hours. To the mixture was added saturated sodium bicarbonate solution (66 mL). The layers were separated; the aqueous layer was extracted with dichloromethane and the organic layers were washed with water. The organic phase was dried over sodium sulfate, filtered through Celite® and concentrated to dryness giving benzyl (Z)-7-[(1R,2S,3R,5S)-2-(triisopropylsilyloxymethyl)-3-(2-phenylmethoxy)-5-(2-tetrahydropyranyloxy)cyclopentyl]-5-heptanoate (19, $R^1$ is phenyl, $R^2$ and $R^3$ are H, $R^7$ is benzyl and $R^8$ is TIPS) quantitatively as a colorless oil.

$^1$H NMR (CDCl$_3$): δ 1.10-0.94 (m, 21H), 2.27-1.50 (m, 16H), 2.37-2.30 (m, 2H), 3.52-3.44 (m, 1H), 3.70-3.64 (m, 1H), 3.99-3.77 (m, 3H), 4.20-4.03 (m, 1H), 4.56-4.41 (m, 2H), 4.71-4.58 (m, 1H), 5.10 (s, 2H), 5.55-5.33 (m, 2H), 7.36-7.27 (m, 10H).

Example 21

Preparation of benzyl (Z)-7-[(1R,2S,3R,5S)-2-hydroxymethyl-3-(2-phenylmethoxy)-5-(2-tetrahydropyranyloxy)cyclopentyl]-5-heptanoate (20, $R^1$ is phenyl, $R^2$ and $R^3$ are H and $R^7$ is benzyl): To a solution of benzyl (Z)-7-[(1R,2S,3R, 5S)-2-(triisopropylsilyloxymethyl)-3-(2-phenylmethoxy)-5-(2-tetrahydropyranyloxy)cyclopentyl]-5-heptanoate (19, $R^1$ is phenyl, $R^2$ and $R^3$ are H, $R^7$ is benzyl and $R^8$ is TIPS, 11.16 mmoL) in tetrahydrofuran (40 mL) at 0-5° C. was added TBAF (1.0 M in tetrahydrofuran, 16.7 mL). The solution was stirred at 0-5° C. for 17 hours then concentrated to dryness. Column chromatography (20% ethyl acetate to 40% ethyl acetate in heptane) yielded benzyl (Z)-7-[(1R,2S,3R,5S)-2-hydroxymethyl-3-(2-phenylmethoxy)-5-(2-tetrahydropyranyloxy)cyclopentyl]-5-heptanoate (20, $R^1$ is phenyl, $R^2$ and $R^3$ are H and $R^7$ is benzyl) as a colourless oil (5.50 g, 94%).

$^1$H NMR (CDCl$_3$): δ 1.87-1.41 (m, 8H), 1.96-1.91 (m, 1H), 2.30-1.97 (m, 6H), 2.38-2.32 (m, 3H), 3.60-3.45 (m, 2H), 4.20-3.62 (m, 4H), 4.44 (dd, 1H, J=5.53, 11.8), 4.70-4.53 (m, 2H), 5.11 (s, 2H), 5.59-5.32 (m, 2H), 7.36-7.24 (m, 10H).

Example 22

Preparation of benzyl (Z)-7-[(1R,2S,3R,5S)-2-formyl-3-(2-phenylmethoxy)-5-(2-tetrahydropyranyloxy)cyclopentyl]-5-heptanoate (21, $R^1$ is phenyl, $R^2$ and $R^3$ are H and $R^7$ is benzyl): To a solution of (COCl)$_2$ (0.66 mL, 7.60 mmoL) in dichloromethane (33 mL) at −78° C. was added DMSO (0.90 mL, 12.66 mmoL). The resulting solution was stirred in at about −78° C. for 10-20 minutes followed by the dropwise addition of benzyl (Z)-7-[(1R,2S,3R,5S)-2-hydroxymethyl-3-(2-phenylmethoxy)-5-(2-tetrahydropyranyloxy)cyclopentyl]-5-heptanoate (20, $R^1$ is phenyl, $R^2$ and $R^3$ are H and $R^7$ is benzyl, 3.31 g, 6.33 mmoL) in dichloromethane (33 mL). The reaction mixture was stirred at −78° C. for 45 minutes at which time triethylamine (2.64 mL, 19.00 mmoL) was charged. After stirring at −78° C. for 4 hours the mixture was quenched with saturated aqueous ammonium chloride and warmed to 20-25° C. The layers were separated; the aqueous layer extracted with dichloromethane and the organic layers washed with saturated aqueous ammonium chloride. The organic phase was dried over sodium sulfate, filtered through Celite® and concentrated to dryness giving benzyl (Z)-7-[(1R,2S,3R,5S)-2-formyl-3-(2-phenylmethoxy)-5-(2-tetrahydropyranyloxy)cyclopentyl]-5-heptanoate (21, $R^1$ is phenyl, $R^2$ and $R^3$ are H and $R^7$ is benzyl) as a pale yellow oil (3.29 g, 99%).

$^1$H NMR (CDCl$_3$): δ 1.84-1.43 (m, 8H), 2.47-1.94 (m, 9H), 2.98-2.86 (m, 1H), 3.54-3.45 (m, 1H), 4.24-3.78 (m, 3H), 4.54-4.42 (m, 2H), 4.70-4.60 (m, 1H), 5.11 (s, 2H), 5.49-5.32 (m, 2H), 7.39-7.24 (m, 10H), 9.73 (dd, 1H, J=2.3, 8.1 Hz).

Example 23

Preparation of benzyl (Z)-7-[(1R,2R,3R,5S)-5-(2-tetrahydropyranyloxy)-2-((E)-4,4-difluoro-3-oxo-1-octenyl)-3-(phenylmethoxy)cyclopentyl]heptanoate (22, $R^1$ is phenyl, $R^2$ and $R^3$ are H and $R^7$ is benzyl): Lithium hydroxide monohydrate (153 mg, 3.635 mmoL) was added to dimethyl(3,3-difluoro-2-oxoheptyl)phosphonate (984 mg, 3.808 mmoL) in methyl t-butyl ether (12 mL) and stirred for 2 hours at 20-25° C. A solution of benzyl (Z)-7-[(1R,2S,3R,5S)-2-formyl-3-(2-phenylmethoxy)-5-(2-tetrahydropyranyloxy)cyclopentyl]-5-heptanoate (21, $R^1$ is phenyl, $R^2$ and $R^3$ are H and $R^7$ is benzyl, 1.8 g, 3.462 mmoL) in dichloromethane (12 mL) was added. The mixture was heated to reflux and stirred for 3 days. To the mixture was added saturated ammonium chloride (10 mL). The layers were separated; the aqueous layer was extracted with dichloromethane, the combined organic layers were dried over sodium sulfate, filtered through Celite® and concentrated to dryness. Column chromatography (100% heptane to 20% ethyl acetate in heptane) gave benzyl (Z)-7-[(1R,2R,3R,5S)-5-(2-tetrahydropyranyloxy)-2-((E)-4,4-difluoro-3-oxo-1-octenyl)-3-(phenylmethoxy)cyclopentyl]heptanoate (22, $R^1$ is phenyl, $R^2$ and $R^3$ are H and $R^7$ is benzyl) as a yellow oil (0.24 g, 11%).

$^1$H NMR (CDCl$_3$): δ 0.91 (t, 3H, J=7.0 Hz), 2.42-1.30 (m, 23H), 2.90-2.75 (m, 1H), 3.49-3.45 (m, 1H), 4.22-3.78 (m, 3H), 4.55-4.41 (m, 2H), 4.71-4.58 (m, 1H), 5.10 (s, 2H), 5.46-5.29 (m, 2H), 6.61 (d, 1H, J=15.7 Hz), 7.12-7.02 (m, 1H), 7.36-7.23 (m, 10H).

Example 24

Preparation of benzyl (Z)-7-[(1R,2R,3R,5S)-5-hydroxy-2-((E)-4,4-difluoro-3-oxo-1-octenyl)-3-(phenylmethoxy)cyclopentyl]heptanoate (23, $R^1$ is phenyl, $R^2$ and $R^3$ are H and $R^7$ is benzyl): Pyridinium p-toluenesulfonate (0.014 g, 0.056 mmoL) was added to a solution of benzyl (Z)-7-[(1R,2R,3R,5S)-5-(2-tetrahydropyranyloxy)-2-((E)-4,4-difluoro-3-oxo-1-octenyl)-3-(phenylmethoxy)cyclopentyl]heptanoate (22, $R^1$ is phenyl, $R^2$ and $R^3$ are H and $R^7$ is benzyl, 0.11 g, 0.169 mmoL) in ethanol (2 mL) at 0-5° C. and was then heated to 40° C. for 18 hours. The ethanol was removed under reduced pressure distillation. To the mixture was added ethyl acetate (5 mL) and saturated aqueous sodium bicarbonate (5 mL). The layers were separated; the aqueous layer was extracted with ethyl acetate, the combined organic layers washed with water, the organic phase was dried over sodium sulfate, filtered through Celite® and concentrated to dryness giving benzyl (Z)-7-[(1R,2R,3R,5S)-5-hydroxy-2-((E)-4,4-difluoro-3-oxo-1-octenyl)-3-(phenylmethoxy)cyclopentypeptanoate (23, $R^1$ is phenyl, $R^2$ and $R^3$ are H and $R^7$ is benzyl) as a yellow oil (0.09 g, 95%).

$^1$H NMR (CDCl$_3$): δ 0.92 (t, 3H, J=7.1 Hz), 1.51-1.32 (m, 4H), 1.75-1.62 (m, 3H), 2.15-1.93 (m, 8H), 2.38-2.29 (m, 3H), 2.79-2.72 (m, 1H), 3.92-3.89 (m, 1H), 4.18-4.15 (m, 1H), 4.53-4.46 (m, 2H), 5.11 (s, 2H), 5.41-5.34 (m, 2H), 6.56 (d, 1H, J=15.2 Hz), 7.05 (dd, 1H, J=9.3, 15.6 Hz), 7.38-7.24 (m, 10H).

Example 25

Preparation of (5Z)-benzyl 7-[(1R,2R,3R)-3-benzyloxy-2-[(E)-4,4-difluoro-3-oxooct-1-enyl]-5-oxocyclopentyl]hept-5-enoate (18, $R^1$ is phenyl, $R^2$ and $R^3$ are H and $R^7$ is benzyl): To a solution of benzyl (Z)-7-[(1R,2R,3R,5S)-5-hydroxy-2-((E)-4,4-difluoro-3-oxo-1-octenyl)-3-(phenylmethoxy)cyclopentypeptanoate (23, $R^1$ is phenyl, $R^2$ and $R^3$ are H and $R^7$ is benzyl, 0.09 g, 0.158 mmoL) in dichloromethane (5 mL) at 0-5° C. was added Dess-Martin periodinane reagent (0.15 g, 0.348 mmoL). The mixture was allowed to warm to room temperature over 2-3 hours. The reaction mixture was quenched with saturated sodium bicarbonate (5 mL). The layers were separated; the organic layer was washed with brine, dried over sodium sulfate, filtered through Celite® and concentrated to dryness to obtain the crude material, which was purified by column chromatography (20%, ethyl acetate in heptanes) to obtain compound (5Z)-benzyl 7-[(1R,2R,3R)-3-benzyloxy-2-[(E)-4,4-difluoro-3-oxooct-1-enyl]-5-oxocyclopentyl]hept-5-enoate (18, $R^1$ is phenyl, $R^2$ and $R^3$ are H and $R^7$ is benzyl) as thick syrup in 80% yield.

$^1$H NMR (CDCl$_3$): δ 0.91 (t, 3H, J=7.0 Hz), 1.50-1.31 (m, 4H), 1.73-1.63 (m, 2H), 2.09-1.92 (m, 4H), 2.42-2.16 (m, 6H), 2.90-2.73 (m, 2H), 3.93 (q, 1H, J=8.1 Hz), 4.53 (m, 2H), 5.10 (s, 2H), 5.47-5.20 (m, 2H), 6.66 (d, 1H, J=16.4 Hz), 7.10 (dd, 1H, J=8.4, 15.6 Hz), 7.35-7.25 (m, 10H).

Example 26

Preparation of Lubiprostone (1): To a solution of (Z)-7-[(1R,2R,3R)-2-((E)-4,4-difluoro-3-oxo-1-octenyl)-3-(phenylmethoxy)-5-oxocyclopentyl]-5-heptenoic acid (10, $R^1$ is phenyl, $R^2$ and $R^3$ are H, $R^6$ is H, and the S/D bond between the carbon at position 9b1 and the carbon at position 9b2 is a double bond, 50 mg) in ethyl acetate (5 mL), was added 10% palladium on carbon (5 mg) and the suspension was hydrogenated at atmospheric pressure for 10 hours. After the completion of the reaction, the mixture was filtered through Celite® and the crude material was re-crystallized using ethyl acetate/heptanes to yield Lubiprostone as a crystalline material in 70% yield.

HRMS (ESI$^+$) [M+NH$_4$]$^+$ Formula: C$_{20}$H$_{36}$F$_2$NO$_5$: cal m/z: 408.25561 amu. found: 408.25626 amu.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. A process for preparation of Lubiprostone comprising hydrogenation, in the presence of a suitable hydrogenation catalyst, of a compound of Formula 10:

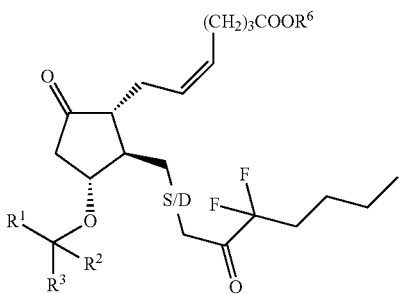

10 wherein R$^1$, R$^2$ and R$^3$ are independently selected from the group consisting of H, alkyl, substituted alkyl, aryl, substituted aryl, arylalkyl, and substituted arylalkyl;
at least one of R$^1$, R$^2$ and R$^3$ is aryl or substituted aryl;
R$^6$ is H or C(R$^{1'}$)(R$^{2'}$)(R$^{3'}$);
R$^{1'}$, R$^{2'}$ and R$^{3'}$ are independently selected from the group consisting of H, alkyl, substituted alkyl, aryl, substituted aryl, arylalkyl, and substituted arylalkyl; and
at least one of R$^{1'}$, R$^{2'}$ and R$^{3'}$ is aryl or substituted aryl;
S/D is a single or a double bond;
wherein
alkyl refers to a straight chain, branched chain or cyclic alkyl group of 1 to 10 carbon atoms, that may be fully saturated, mono- or polyunsaturated;
aryl refers to a polyunsaturated, aromatic hydrocarbon of from 1 to 3 rings that are either fused or covalently linked, optionally containing from 1 to 4 heteroatoms selected from N, O and S, wherein the nitrogen and sulphur atoms are optionally oxidized, and the nitrogen atom is optionally quaternized;
arylalkyl refers to groups in which an aryl group is attached to an alkyl group, optionally where a methylene carbon of the alkyl group is replaced by an oxygen atom; and
the substitution of the alkyl, aryl or arylalkyl group refers to the presence of one or more substituents selected from the group consisting alkyl or alkoxy of from 1 to 10 carbons, halogen, NO$_2$ and trifluoromethyl.

2. The process of claim 1 wherein the hydrogenation is performed using hydrogen gas.

3. The process of claim 1 wherein the suitable hydrogenation catalyst is selected from the group consisting of palladium, platinum, rhodium, ruthenium, and Raney-nickel.

4. The process of claim 1 wherein the suitable hydrogenation catalyst is palladium on carbon.

5. The process of claim 4 wherein the suitable hydrogenation catalyst is 10 wt % palladium on carbon (dry basis), 50 wt % (wet support).

6. The process of claim 1 wherein the S/D is a double bond.

7. The process of claim 1 wherein the compound of Formula 10 is a compound of Formula 18:

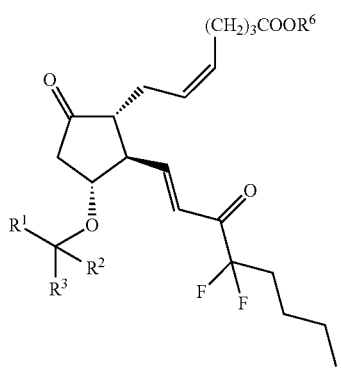

18 wherein R$^1$, R$^2$ and R$^3$ are independently selected from the group consisting of H, alkyl, substituted alkyl, aryl, substituted aryl, arylalkyl, and substituted arylalkyl;
at least one of R$^1$, R$^2$ and R$^3$ is aryl or substituted aryl;
R$^6$ is H or C(R$^{1'}$)(R$^{2'}$)(R$^{3'}$);
R$^{1'}$, R$^{2'}$ and R$^{3'}$ are independently selected from the group consisting of H, alkyl, substituted alkyl, aryl, substituted aryl, arylalkyl, and substituted arylalkyl; and
at least one of R$^{1'}$, R$^{2'}$ and R$^{3'}$ is aryl or substituted aryl;
wherein
alkyl refers to a straight chain, branched chain or cyclic alkyl group of 1 to 10 carbon atoms, that may be fully saturated, mono- or polyunsaturated;
aryl refers to a polyunsaturated, aromatic hydrocarbon of from 1 to 3 rings that are either fused or covalently linked, optionally containing from 1 to 4 heteroatoms selected from N, O and S, wherein the nitrogen and sulphur atoms are optionally oxidized, and the nitrogen atom is optionally quaternized;

arylalkyl refers to groups in which an aryl group is attached to an alkyl group, optionally where a methylene carbon of the alkyl group is replaced by an oxygen atom; and the substitution of the alkyl, aryl or arylalkyl group refers to the presence of one or more substituents selected from the group consisting of alkyl or alkoxy of from 1 to 10 carbons, halogen, $NO_2$ and trifluoromethyl.

8. The process of claim 7 wherein the compound of Formula 18 is a compound of Formula 18a:

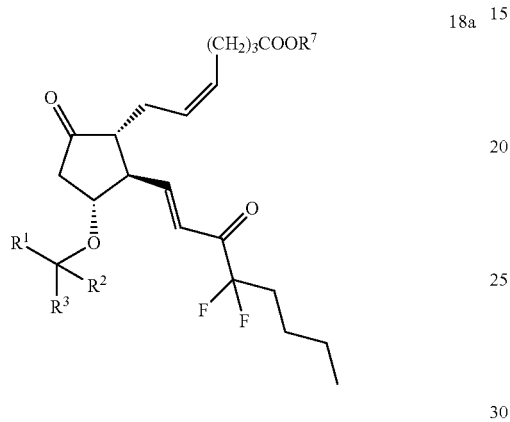

18a wherein $R^1$, $R^2$ and $R^3$ are independently selected from the group consisting of H, alkyl, substituted alkyl, aryl, substituted aryl, arylalkyl, and substituted arylalkyl;

at least one of $R^1$, $R^2$ and $R^3$ is aryl or substituted aryl;

$R^7$ is $C(R^{1'})(R^{2'})(R^{3'})$;

$R^{1'}$, $R^{2'}$ and $R^{3'}$ are independently selected from the group consisting of H, alkyl, substituted alkyl, aryl, substituted aryl, arylalkyl, and substituted arylalkyl; and at least one of $R^{1'}$, $R^{2'}$ and $R^{3'}$ is aryl or substituted aryl;

wherein
alkyl refers to a straight chain, branched chain or cyclic alkyl group of 1 to 10 carbon atoms, that may be fully saturated, mono- or polyunsaturated;

aryl refers to a polyunsaturated, aromatic hydrocarbon of from 1 to 3 rings that are either fused or covalently linked, optionally containing from 1 to 4 heteroatoms selected from N, O and S, wherein the nitrogen and sulphur atoms are optionally oxidized, and the nitrogen atom is optionally quaternized;

arylalkyl refers to groups in which an aryl group is attached to an alkyl group, optionally where a methylene carbon of the alkyl group is replaced by an oxygen atom; and the substitution of the alkyl, aryl or arylalkyl group refers to the presence of one or more substituents selected from the group consisting of alkyl or alkoxy of from 1 to 10 carbons, halogen, $NO_2$ and trifluoromethyl.

9. The process of claim 8 wherein the compound of Formula 18a is prepared by reacting, in the presence of a seventh base selected from the group consisting of: alkali hydroxides, $Zn(OH)_2$, mixtures of ammonia and alkali hydroxides, and mixtures thereof, a compound of Formula 17a:

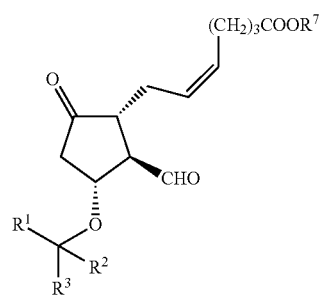

17a with a compound of Formula 12:

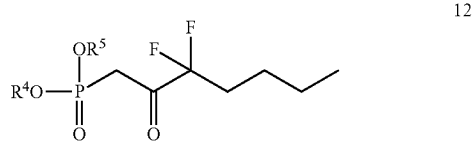

12 wherein $R^1$, $R^2$ and $R^3$ are independently selected from the group consisting of H, alkyl, substituted alkyl, aryl, substituted aryl, arylalkyl, and substituted arylalkyl;

at least one of $R^1$, $R^2$ and $R^3$ is aryl or substituted aryl;

$R^4$ and $R^5$ are independently a short chain alkyl;

$R^7$ is $C(R^{1'})(R^{2'})(R^{3'})$;

$R^{1'}$, $R^{2'}$ and $R^{3'}$ are independently selected from the group consisting of H, alkyl, substituted alkyl, aryl, substituted aryl, arylalkyl, and substituted arylalkyl; and at least one of $R^{1'}$, $R^{2'}$ and $R^{3'}$ is aryl or substituted aryl;

wherein
alkyl refers to a straight chain, branched chain or cyclic alkyl group of 1 to 10 carbon atoms, that may be fully saturated, mono- or polyunsaturated;

aryl refers to a polyunsaturated, aromatic hydrocarbon of from 1 to 3 rings that are either fused or covalently linked, optionally containing from 1 to 4 heteroatoms selected from N, O and S, wherein the nitrogen and sulphur atoms are optionally oxidized, and the nitrogen atom is optionally quaternized;

arylalkyl refers to groups in which an aryl group is attached to an alkyl group, optionally where a methylene carbon of the alkyl group is replaced by an oxygen atom; and the substitution of the alkyl, aryl or arylalkyl group refers to the presence of one or more substituents selected from the group consisting of alkyl or alkoxy of from 1 to 10 carbons, halogen, $NO_2$ and trifluoromethyl.

10. The process of claim 9 wherein the compound of Formula 17a is prepared by oxidizing a compound of Formula 16a:

53

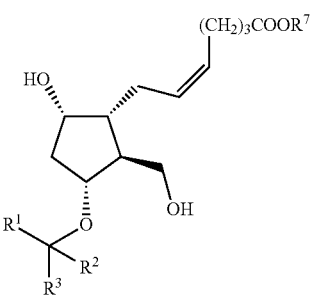

16a wherein $R^1$, $R^2$ and $R^3$ are independently selected from the group consisting of H, alkyl, substituted alkyl, aryl, substituted aryl, arylalkyl, and substituted arylalkyl;
at least one of $R^1$, $R^2$ and $R^3$ is aryl or substituted aryl;
$R^7$ is $C(R^{1'})(R^{2'})(R^{3'})$;
$R^{1'}$, $R^{2'}$ and $R^{3'}$ are independently selected from the group consisting of 1-1, alkyl, substituted alkyl, aryl, substituted aryl, arylalkyl, and substituted arylalkyl; and
at least one of $R^{1'}$, $R^{2'}$ and $R^{3'}$ is aryl or substituted aryl;
wherein
alkyl refers to a straight chain, branched chain or cyclic alkyl group of 1 to 10 carbon atoms, that may be fully saturated, mono- or polyunsaturated;
aryl refers to a polyunsaturated, aromatic hydrocarbon of from 1 to 3 rings that are either fused or covalently linked, optionally containing from 1 to 4 heteroatoms selected from N, O and S, wherein the nitrogen and sulphur atoms are optionally oxidized, and the nitrogen atom is optionally quaternized;
arylalkyl refers to groups in which an aryl group is attached to an alkyl group, optionally where a methylene carbon of the alkyl group is replaced by an oxygen atom; and
the substitution of the alkyl, aryl or arylalkyl group refers to the presence of one or more substituents selected from the group consisting of alkyl or alkoxy of from 1 to 10 carbons, halogen, $NO_2$ and trifluoromethyl.

11. The process of claim 10 wherein the compound of Formula 16a is prepared by deprotection of a compound of Formula 15:

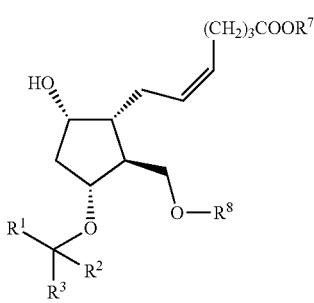

15 wherein $R^1$, $R^2$ and $R^3$ are independently selected from the group consisting of H, alkyl, substituted alkyl, aryl, substituted aryl, arylalkyl, and substituted arylalkyl;
at least one of $R^1$, $R^2$ and $R^3$ is aryl or substituted aryl;
$R^7$ is $C(R^{1'})(R^{2'})(R^{3'})$;
$R^{1'}$, $R^{2'}$ and $R^{3'}$ are independently selected from the group consisting of H, alkyl, substituted alkyl, aryl, substituted aryl, arylalkyl, and substituted arylalkyl;

54 at least one of $R^{1'}$, $R^{2'}$ and $R^{3'}$ is aryl or substituted aryl; and
$R^8$ is a silyl protecting group;
wherein
alkyl refers to a straight chain, branched chain or cyclic alkyl group of 1 to 10 carbon atoms, that may be fully saturated, mono- or polyunsaturated;
aryl refers to a polyunsaturated, aromatic hydrocarbon of from 1 to 3 rings that are either fused or covalently linked, optionally containing from 1 to 4 heteroatoms selected from N, O and S, wherein the nitrogen and sulphur atoms are optionally oxidized, and the nitrogen atom is optionally quaternized;
arylalkyl refers to groups in which an aryl group is attached to an alkyl group, optionally where a methylene carbon of the alkyl group is replaced by an oxygen atom; and
the substitution of the alkyl, aryl or arylalkyl group refers to the presence of one or more substituents selected from the group consisting of alkyl or alkoxy of from 1 to 10 carbons, halogen, $NO_2$ and trifluoromethyl.

12. The process of claim 8 wherein the compound of Formula 18a is prepared by oxidizing a compound of Formula 23:

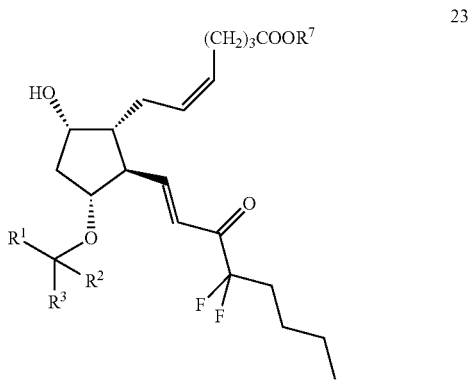

23 wherein $R^1$, $R^2$ and $R^3$ are independently selected from the group consisting of H, alkyl, substituted alkyl, aryl, substituted aryl, arylalkyl, and substituted arylalkyl;
at least one of $R^1$, $R^2$ and $R^3$ is aryl or substituted aryl;
$R^7$ is $C(R^{1'})(R^{2'})(R^{3'})$;
$R^{1'}$, $R^{2'}$ and $R^{3'}$ are independently selected from the group consisting of H, alkyl, substituted alkyl, aryl, substituted aryl, arylalkyl, and substituted arylalkyl; and
at least one of $R^{1'}$, $R^{2'}$ and $R^{3'}$ is aryl or substituted aryl;
wherein
alkyl refers to a straight chain, branched chain or cyclic alkyl group of 1 to 10 carbon atoms, that may be fully saturated, mono- or polyunsaturated;
aryl refers to a polyunsaturated, aromatic hydrocarbon of from 1 to 3 rings that are either fused or covalently linked, optionally containing from 1 to 4 heteroatoms selected from N, O and S, wherein the nitrogen and sulphur atoms are optionally oxidized, and the nitrogen atom is optionally quaternized;
arylalkyl refers to groups in which an aryl group is attached to an alkyl group, optionally where a methylene carbon of the alkyl group is replaced by an oxygen atom; and
the substitution of the alkyl, aryl or arylalkyl group refers to the presence of one or more substituents selected from the group consisting of alkyl or alkoxy of from 1 to 10 carbons, halogen, $NO_2$ and trifluoromethyl.

13. The process of claim 12 wherein oxidizing comprises using an oxidizing agent selected from the group consisting of: Dess-Martin periodinane, $CrO_3$, $MnO_2$, 2,2,6,6-tetramethyl-piperidinyloxy free radical/sodium hypochlorite, $SO_3$/pyridine and oxalyl chloride/dimethylsulfoxide/triethylamine.

14. The process of claim 13 wherein the oxidizing agent is Dess-Martin periodinane.

15. The process of claim 12 wherein oxidizing comprises using a eighth solvent selected from the group consisting of: dichloromethane, dimethylsulfoxide, and mixtures thereof.

16. The process of claim 11 wherein the compound of Formula 15 is prepared by reacting, in the presence of a ninth base selected from the group consisting of triethylamine, diisopropylamine, diisopropylethylamine, pyridine and 1,8-Diazabicyclo[5.4.0]undec-7-ene, a compound of having a structure of $R^7$-G, wherein G is a leaving group and $R^7$ is $C(R^{1'})(R^{2'})(R^{3'})$, with a compound of Formula 14:

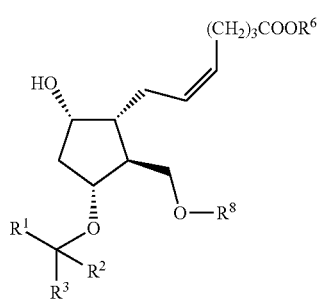

14 wherein $R^1$, $R^2$ and $R^3$ are independently selected from the group consisting of H, alkyl, substituted alkyl, aryl, substituted aryl, arylalkyl, and substituted arylalkyl;
at least one of $R^1$, $R^2$ and $R^3$ is aryl or substituted aryl;
$R^6$ is H; and
$R^8$ is a silyl protecting group;
wherein
alkyl refers to a straight chain, branched chain or cyclic alkyl group of 1 to 10 carbon atoms, that may be fully saturated, mono- or polyunsaturated;
aryl refers to a polyunsaturated, aromatic hydrocarbon of from 1 to 3 rings that are either fused or covalently linked, optionally containing from 1 to 4 heteroatoms selected from N, O and S, wherein the nitrogen and sulphur atoms are optionally oxidized, and the nitrogen atom is optionally quaternized;
arylalkyl refers to groups in which an aryl group is attached to an alkyl group, optionally where a methylene carbon of the alkyl group is replaced by an oxygen atom; and
the substitution of the alkyl, aryl or arylalkyl group refers to the presence of one or more substituents selected from the group consisting of alkyl or alkoxy of from 1 to 10 carbons, halogen, $NO_2$ and trifluoromethyl.

17. The process of claim 16 wherein G is selected from the group consisting of: chlorine, bromine, iodine, methansulfonyloxy, trifluoromethansulfonyloxy and p-toluenesulfonyloxy.

18. The process of claim 16 wherein $R^7$-G is a benzyl halide.

19. The process of claim 16 wherein the ninth base is selected from the group consisting of: triethylamine, diisopropylamine, pyridine and 1,8-Diazabicyclo[5.4.0]undec-7-ene.

20. The process of claim 1 wherein the compound of Formula 10 is prepared by oxidation of a compound of Formula 9:

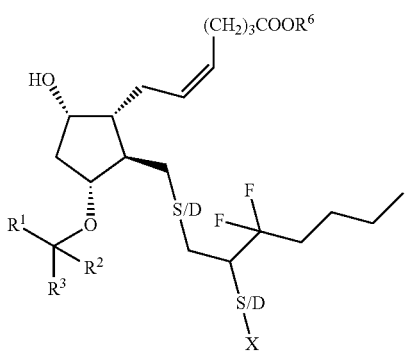

9 wherein $R^1$, $R^2$ and $R^3$ are independently selected from the group consisting of H, alkyl, substituted alkyl, aryl, substituted aryl, arylalkyl, and substituted arylalkyl;
at least one of $R^1$, $R^2$ and $R^3$ is aryl or substituted aryl;
$R^6$ is H or $C(R^{1'})(R^{2'})(R^{3'})$;
$R^{1'}$, $R^{2'}$ and $R^{3'}$ are independently selected from the group consisting of H, alkyl, substituted alkyl, aryl, substituted aryl, arylalkyl, and substituted arylalkyl;
at least one of $R^{1'}$, $R^{2'}$ and $R^{3'}$ is aryl or substituted aryl;
X is OH or O; and
each S/D is independently a single or a double bond;
wherein
alkyl refers to a straight chain, branched chain or cyclic alkyl group of 1 to 10 carbon atoms, that may be fully saturated, mono- or polyunsaturated;
aryl refers to a polyunsaturated, aromatic hydrocarbon of from 1 to 3 rings that are either fused or covalently linked, optionally containing from 1 to 4 heteroatoms selected from N, O and S, wherein the nitrogen and sulphur atoms are optionally oxidized, and the nitrogen atom is optionally quaternized;
arylalkyl refers to groups in which an aryl group is attached to an alkyl group, optionally where a methylene carbon of the alkyl group is replaced by an oxygen atom; and
the substitution of the alkyl, aryl or arylalkyl group refers to the presence of one or more substituents selected from the group consisting of alkyl or alkoxy of from 1 to 10 carbons, halogen, $NO_2$ and trifluoromethyl.

21. The process of claim 20 wherein oxidation is performed using an oxidizing agent selected from the group consisting of Dess-Martin periodinane, o-iodoxybenzoic acid, $CrO_3$, $MnO_2$, 2,2,6,6-tetramethyl-piperidinyloxy free radical/sodium hypochlorite and $SO_3$/pyridine.

22. The process of claim 20 wherein oxidation is conducted in a fourth solvent, the fourth solvent comprising dichloromethane.

23. The process of any one of claims 1 or 20 wherein the compound of Formula 10 that is hydrogenated to Lubiprostone is a compound of Formula 10a:

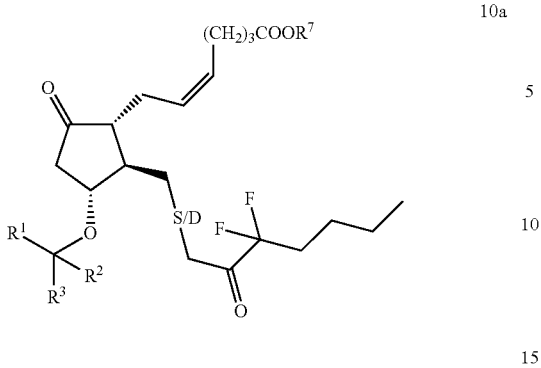

wherein R¹, R² and R³ are independently selected from the group consisting of H, alkyl, substituted alkyl, aryl, substituted aryl, arylalkyl, and substituted arylalkyl;

at least one of R¹, R² and R³ is aryl or substituted aryl;

R⁷ is C(R¹')(R²')(R³');

R¹', R²' and R³' are independently selected from the group consisting of H, alkyl, substituted alkyl, aryl, substituted aryl, arylalkyl, and substituted arylalkyl;

at least one of R¹', R²' and R³' is aryl or substituted aryl; and

S/D is a single or a double bond;

wherein
  alkyl refers to a straight chain, branched chain or cyclic alkyl group of 1 to 10 carbon atoms, that may be fully saturated, mono- or polyunsaturated;
  aryl refers to a polyunsaturated, aromatic hydrocarbon of from 1 to 3 rings that are either fused or covalently linked, optionally containing from 1 to 4 heteroatoms selected from N, O and S, wherein the nitrogen and sulphur atoms are optionally oxidized, and the nitrogen atom is optionally quaternized;
  arylalkyl refers to groups in which an aryl group is attached to an alkyl group, optionally where a methylene carbon of the alkyl group is replaced by an oxygen atom; and
  the substitution of the alkyl, aryl or arylalkyl group refers to the presence of one or more substituents selected from the group consisting of alkyl or alkoxy of from 1 to 10 carbons, halogen, NO₂ and trifluoromethyl.

24. The process of any one of claims 1, 7, 8, 9, 10, 11, 12, and 20 wherein hydrogenation comprises using ethyl acetate.

25. The process of any one of claims 1 and 20 wherein the S/D bond between carbon 9b1 and carbon 9b2 of the compound of Formula 10 is a single bond.

26. The process of any one of claims 1 and 20 wherein the S/D bond between carbon 9b1 and carbon 9b2 of the compound of Formula 10 is a double bond.

27. The process of any one of claims 1 and 20 wherein the reaction comprises a mixture of compounds of Formula 10 wherein the mixture comprises compounds in which the S/D bond between carbon 9b1 and carbon 9b2 is a single bond and compounds in which the S/D bond between carbon 9b1 and carbon 9b2 is a double bond.

28. A compound of Formula 15:

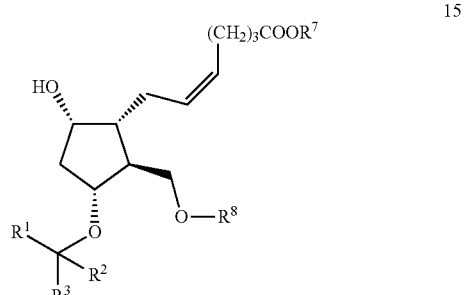

wherein R¹, R² and R³ are independently selected from the group consisting of H, alkyl, substituted alkyl, aryl, substituted aryl, arylalkyl, and substituted arylalkyl;

at least one of R¹, R² and R³ is aryl or substituted aryl;

R⁷ is C(R¹')(R²')(R³'), where R¹', R²' and R³' are independently selected from the group consisting of H, alkyl, substituted alkyl, aryl, substituted aryl, arylalkyl, and substituted arylalkyl;

at least one of R¹', R²' and R³' is aryl or substituted aryl; and

R⁸ is a silyl protecting group;

wherein
  alkyl refers to a straight chain, branched chain or cyclic alkyl group of 1 to 10 carbon atoms, that may be fully saturated, mono- or polyunsaturated;
  aryl refers to a polyunsaturated, aromatic hydrocarbon of from 1 to 3 rings that are either fused or covalently linked, optionally containing from 1 to 4 heteroatoms selected from N, O and S, wherein the nitrogen and sulphur atoms are optionally oxidized, and the nitrogen atom is optionally quaternized;
  arylalkyl refers to groups in which an aryl group is attached to an alkyl group, optionally where a methylene carbon of the alkyl group is replaced by an oxygen atom; and
  the substitution of the alkyl, aryl or arylalkyl group refers to the presence of one or more substituents selected from the group consisting of alkyl or alkoxy of from 1 to 10 carbons, halogen, NO₂ and trifluoromethyl.

29. A compound of Formula 16a:

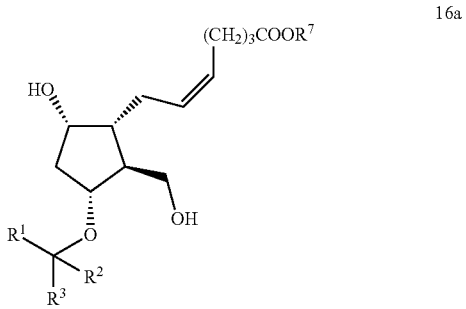

wherein R¹, R² and R³ are independently selected from the group consisting of H, alkyl, substituted alkyl, aryl, substituted aryl, arylalkyl, and substituted arylalkyl;

at least one of R¹, R² and R³ is aryl or substituted aryl;

R⁷ is C(R¹')(R²')(R³'), where R¹', R²' and R³' are independently selected from the group consisting of H, alkyl, substituted alkyl, aryl, substituted aryl, arylalkyl, and substituted arylalkyl; and at least one of $R^{1'}$, $R^{2'}$ and $R^{3'}$ is aryl or substituted aryl; wherein alkyl refers to a straight chain, branched chain or cyclic alkyl group of 1 to 10 carbon atoms, that may be fully saturated, mono- or polyunsaturated;

aryl refers to a polyunsaturated, aromatic hydrocarbon of from 1 to 3 rings that are either fused or covalently linked, optionally containing from 1 to 4 heteroatoms selected from N, O and S, wherein the nitrogen and sulphur atoms are optionally oxidized, and the nitrogen atom is optionally quaternized;

arylalkyl refers to groups in which an aryl group is attached to an alkyl group, optionally where a methylene carbon of the alkyl group is replaced by an oxygen atom; and the substitution of the alkyl, aryl or arylalkyl group refers to the presence of one or more substituents selected from the group consisting of alkyl or alkoxy of from 1 to 10 carbons, halogen, $NO_2$ and trifluoromethyl.

30. A compound of Formula 17a:

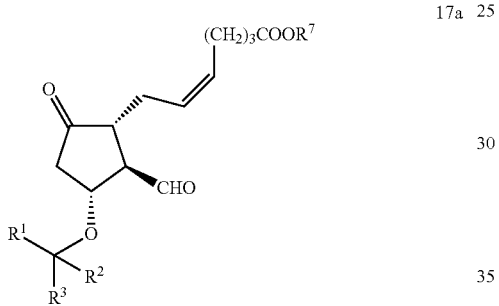

wherein $R^1$, $R^2$ and $R^3$ are independently selected from the group consisting of H, alkyl, substituted alkyl, aryl, substituted aryl, arylalkyl, and substituted arylalkyl;

at least one of $R^1$, $R^2$ and $R^3$ is aryl or substituted aryl;

$R^7$ is $C(R^{1'})(R^{2'})(R^{3'})$, where $R^{1'}$, $R^{2'}$ and $R^{3'}$ are independently selected from the group consisting of H, alkyl, substituted alkyl, aryl, substituted aryl, arylalkyl, and substituted arylalkyl; and at least one of $R^{1'}$, $R^{2'}$ and $R^{3'}$ is aryl or substituted aryl; wherein alkyl refers to a straight chain, branched chain or cyclic alkyl group of 1 to 10 carbon atoms, that may be fully saturated, mono- or polyunsaturated;

aryl refers to a polyunsaturated, aromatic hydrocarbon of from 1 to 3 rings that are either fused or covalently linked, optionally containing from 1 to 4 heteroatoms selected from N, O and S, wherein the nitrogen and sulphur atoms are optionally oxidized, and the nitrogen atom is optionally quaternized;

arylalkyl refers to groups in which an aryl group is attached to an alkyl group, optionally where a methylene carbon of the alkyl group is replaced by an oxygen atom; and the substitution of the alkyl, aryl or arylalkyl group refers to the presence of one or more substituents selected from the group consisting of alkyl or alkoxy of from 1 to 10 carbons, halogen, $NO_2$ and trifluoromethyl.

31. A compound of Formula 18a:

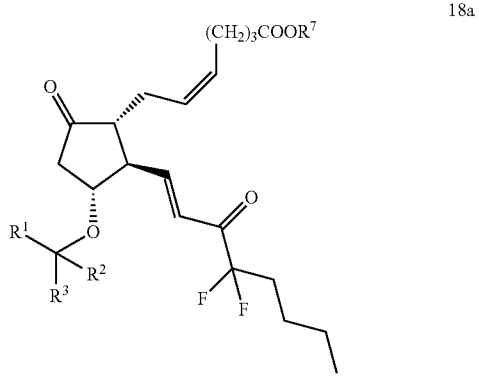

wherein $R^1$, $R^2$ and $R^3$ are independently selected from the group consisting of H, alkyl, substituted alkyl, aryl, substituted aryl, arylalkyl, and substituted arylalkyl;

at least one of $R^1$, $R^2$ and $R^3$ is aryl or substituted aryl;

$R^7$ is $C(R^{1'})(R^{2'})(R^{3'})$, where $R^{1'}$, $R^{2'}$ and $R^{3'}$ are independently selected from the group consisting of H, alkyl, substituted alkyl, aryl, substituted aryl, arylalkyl, and substituted arylalkyl; and at least one of $R^{1'}$, $R^{2'}$ and $R^{3'}$ is aryl or substituted aryl; wherein alkyl refers to a straight chain, branched chain or cyclic alkyl group of 1 to 10 carbon atoms, that may be fully saturated, mono- or polyunsaturated;

aryl refers to a polyunsaturated, aromatic hydrocarbon of from 1 to 3 rings that are either fused or covalently linked, optionally containing from 1 to 4 heteroatoms selected from N, O and S, wherein the nitrogen and sulphur atoms are optionally oxidized, and the nitrogen atom is optionally quaternized;

arylalkyl refers to groups in which an aryl group is attached to an alkyl group, optionally where a methylene carbon of the alkyl group is replaced by an oxygen atom; and the substitution of the alkyl, aryl or arylalkyl group refers to the presence of one or more substituents selected from the group consisting of alkyl or alkoxy of from 1 to 10 carbons, halogen, $NO_2$ and trifluoromethyl.

32. A compound selected from the group consisting of: (3aR,4S,5R,6aS)-5-(phenylmethoxy)-4-(triisopropylsilyloxymethyl)hexahydrocyclopenta[b]furan-2-ol; (5Z)-7-[(1R,2S,3R,5S)-3-Benzyloxy-5-hydroxy-2-[(triisopropylsilyloxy)methyl]cyclopentyl]hept-5-enoic acid; Benzyl (Z)-7-[(1R,2S,3R,5S)-5-hydroxy-3-(2-phenylmethoxy)-2-(triisopropylsilyloxymethyl)cyclopentyl]-5-heptanoate; (5Z)-Benzyl 7-[(1R,2S,3R,5S)-3-benzyloxy-5-hydroxy-2-(hydroxymethyl)cyclopentyl]hept-5-enoate; (5Z)-Benzyl 7-[(1R,2R,3R)-3-benzyloxy-2-formyl 5-oxocyclopentyl] hept-5-enoate; Benzyl (Z)-7-[(1R,2S,3R,5S)-2-(triisopropylsilyloxymethyl)-3-(2-phenylmethoxy)-5-(2-tetrahydropyranyloxy)cyclopentyl]-5-heptanoate; Benzyl (Z)-7-[(1R,2S,3R,5S)-2-hydroxymethyl-3-(2-phenylmethoxy)-5-(2-tetrahydropyranyloxy)cyclopentyl]-5-heptanoate; Benzyl (Z)-7-[(1R,2S,3R,5S)-2-formyl-3-(2-phenylmethoxy)-5-(2-tetrahydropyranyloxy)cyclopentyl]-5-heptanoate; Benzyl (Z)-7-[(1R,2R,3R,5S)-5-(2-tetrahydropyranyloxy)-2-((E)-3- oxo-1-octenyl)-3-(phenylmethoxy)cyclopentyl]heptanoate; and Benzyl (Z)-7-[(1R,2R,3R,5S)-5-hydroxy-2-((E)-3-oxo-1-octenyl)-3-(phenylmethoxy)cyclopentyl]heptanoate.

33. A compound of Formula 10:

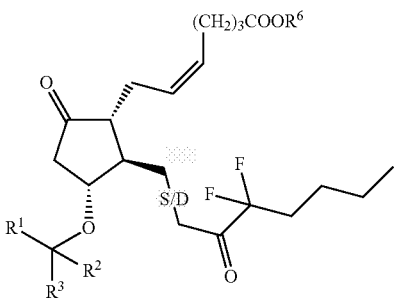

wherein R¹, R² and R³ are independently selected from the group consisting of H, alkyl, substituted alkyl, aryl, substituted aryl, arylalkyl, and substituted arylalkyl;
at least one of R¹, R² and R³ is aryl or substituted aryl;
R⁶ is H or C(R¹')(R²')(R³');
R¹', R²' and R³' are independently selected from the group consisting of H, alkyl, substituted alkyl, aryl, substituted aryl, arylalkyl, and substituted arylalkyl;
at least one of R¹', R²' and R³' is aryl or substituted aryl; and
S/D is a single or a double bond;
wherein
alkyl refers to a straight chain, branched chain or cyclic alkyl group of 1 to 10 carbon atoms, that may be fully saturated, mono- or polyunsaturated;
aryl refers to a polyunsaturated, aromatic hydrocarbon of from 1 to 3 rings that are either fused or covalently linked, optionally containing from 1 to 4 heteroatoms selected from N, O and S, wherein the nitrogen and sulphur atoms are optionally oxidized, and the nitrogen atom is optionally quaternized;
arylalkyl refers to groups in which an aryl group is attached to an alkyl group, optionally where a methylene carbon of the alkyl group is replaced by an oxygen atom; and
the substitution of the alkyl, aryl or arylalkyl group refers to the presence of one or more substituents selected from the group consisting of alkyl or alkoxy of from 1 to 10 carbons, halogen, $NO_2$ and trifluoromethyl.

34. A compound selected from the group consisting of: (3aR,4R,5R,6aS)-hexahydro-2-oxo-5-(phenylmethoxy)-2H-cyclopenta[b]furan-4-carboxaldehyde; (3aR,4R,5R,6aS)-4-((E)-4,4-difluoro-3-oxo-1-octenyl)-2-oxo-5-(phenylmethoxy)hexahydro-2H-cyclopenta[b]furan; (3aR,4R,5R,6aS)-4-(4,4-difluoro-3-oxo-1-octyl)-2-oxo-5-(phenylmethoxy)hexahydro-2H-cyclopenta[b]furan; (3aR,4R,5R,6aS)-4-((E)-4,4-difluoro-3-hydroxy-1-octenyl)-5-(phenylmethoxy)hexahydro-2H-cyclopenta[b]furan-2-ol; (3aR,4R,5R,6aS)-4-((E)-4,4-difluoro-3-oxo-1-octenyl)-5-(phenylmethoxy)hexahydro-2H-cyclopenta[b]furan-2-ol; (3aR,4R,5R,6aS)-4-(4,4-difluoro-3-hydroxy-1-octyl)-5-(phenylmethoxy)hexahydro-2H-cyclopenta[b]furan-2-ol; (3aR,4R,5R,6aS)-4-(4,4-difluoro-3-oxo-1-octyl)-5-(phenylmethoxy)hexahydro-2H-cyclopenta[b]furan-2-ol; (Z)-7-[(1R,2R,3R,5S)-2-((E)-4,4-difluoro-3-hydroxy-1-octenyl)-3-(phenylmethoxy)-5-hydroxycyclopentyl]-5-heptenoic acid; (Z)-7-[(1R,2R,3R,5S)-2-((E)-4,4-difluoro-3-oxo-1-octenyl)-3-(phenylmethoxy)-5-hydroxycyclopentyl]-5-heptenoic acid; (Z)-7-[(1R,2R,3R,5S)-2-(4,4-difluoro-3-hydroxy-1-octyl)-3-(phenylmethoxy)-5-hydroxycyclopentyl]-5-heptenoic acid; (Z)-7-[(1R,2R,3R,5S)-2-(4,4-difluoro-3-oxo-1-octyl)-3-(phenylmethoxy)-5-hydroxycyclopentyl]-5-heptenoic acid; Benzyl (Z)-7-[(1R,2R,3R,5S)-2-((E)-4,4-difluoro-3-hydroxy-1-octenyl)-3-(phenylmethoxy)-5-hydroxycyclopentyl]-5-heptenoate; Benzyl (Z)-7-[(1R,2R,3R,5S)-2-((E)-4,4-difluoro-3-oxo-1-octenyl)-3-(phenylmethoxy)-5-hydroxycyclopentyl]-5-heptenoate; Benzyl (Z)-7-[(1R,2R,3R,5S)-2-(4,4-difluoro-3-hydroxy-1-octyl)-3-(phenylmethoxy)-5-hydroxycyclopentyl]-5-heptenoate; Benzyl (Z)-7-[(1R,2R,3R,5S)-2-(4,4-difluoro-3-oxo-1-octyl)-3-(phenylmethoxy)-5-hydroxycyclopentyl]-5-heptenoate; (Z)-7-[(1R,2R,3R)-2-((E)-4,4-difluoro-3-oxo-1-octenyl)-3-(phenylmethoxy)-5-oxocyclopentyl]-5-heptenoic acid; (Z)-7-[(1R,2R,3R)-2-(4,4-difluoro-3-oxo-1-octyl)-3-(phenylmethoxy)-5-oxocyclopentyl]-5-heptenoic acid; Benzyl (Z)-7-[(1R,2R,3R)-2-((E)-4,4-difluoro-3-oxo-1-octenyl)-3-(phenylmethoxy)-5-oxocyclopentyl]-5-heptenoate; and Benzyl (Z)-7-[(1R,2R,3R)-2-(4,4-difluoro-3-oxo-1-octyl)-3-(phenylmethoxy)-5-oxocyclopentyl]-5-heptenoate.

\* \* \* \* \*